(12) United States Patent
Ju et al.

(10) Patent No.: US 8,796,432 B2
(45) Date of Patent: Aug. 5, 2014

(54) CHEMICALLY CLEAVABLE 3'-O-ALLYL-DNTP-ALLYL-FLUOROPHORE FLUORESCENT NUCLEOTIDE ANALOGUES AND RELATED METHODS

(75) Inventors: Jingyue Ju, Englewood Cliffs, NJ (US); Lanrong Bi, New York, NY (US); Dae H. Kim, New York, NY (US); Qinglin Meng, Sunnyvale, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 344 days.

(21) Appl. No.: 12/084,457

(22) PCT Filed: Oct. 31, 2006

(86) PCT No.: PCT/US2006/042739
§ 371 (c)(1),
(2), (4) Date: Apr. 30, 2008

(87) PCT Pub. No.: WO2007/053719
PCT Pub. Date: May 10, 2007

(65) Prior Publication Data
US 2009/0263791 A1  Oct. 22, 2009

Related U.S. Application Data

(60) Provisional application No. 60/732,040, filed on Oct. 31, 2005.

(51) Int. Cl.
*C07G 11/00* (2006.01)
*C07H 21/00* (2006.01)
*C07H 21/02* (2006.01)
*C12Q 1/68* (2006.01)
*C12P 19/34* (2006.01)
*B01L 3/00* (2006.01)

(52) U.S. Cl.
USPC ......... 536/4.1; 536/23.1; 536/24.3; 536/25.3; 536/26.6; 435/6.1; 435/91.1; 422/430

(58) Field of Classification Search
USPC ........ 536/4.1, 23.1, 24.3, 25.3, 26.6; 435/6.1, 435/91.1; 422/430
See application file for complete search history.

(56) References Cited

U.S. PATENT DOCUMENTS 4,888,274 A  12/1989 Radding et al.
5,547,839 A  8/1996 Dower et al.
(Continued)

FOREIGN PATENT DOCUMENTS

DE  4141178  6/1993
GB  2446083 B  3/2011
(Continued)

OTHER PUBLICATIONS

International Search Report issued by the International Searching Authority (ISA/US) on Feb. 6, 2008 in connection with International Application No. PCT/US2006/042739.

(Continued)

*Primary Examiner* — Jezia Riley
(74) *Attorney, Agent, or Firm* — John P. White; Cooper & Dunham LLP

(57) ABSTRACT

This invention provides a nucleotide analogue comprising (i) a base selected from the group consisting of adenine, guanine, cytosine, thymine and uracil, (ii) a deoxyribose, (iii) an allyl moiety bound to the 3'-oxygen of the deoxyribose and (iv) a fluorophore bound to the base via an allyl linker, and methods of nucleic acid sequencing employing the nucleotide analogue.

19 Claims, 7 Drawing Sheets

(56) References Cited

U.S. PATENT DOCUMENTS

| | | | |
|---|---|---|---|
| 5,804,386 | A | 9/1998 | Ju |
| 5,814,454 | A | 9/1998 | Ju |
| 5,876,936 | A | 3/1999 | Ju |
| 5,952,180 | A | 9/1999 | Ju |
| 6,046,005 | A | 4/2000 | Ju et al. |
| 6,207,831 | B1 | 3/2001 | Auer et al. |
| 6,309,829 | B1 | 10/2001 | Livak et al. |
| 6,627,748 | B1 | 9/2003 | Ju et al. |
| 6,664,079 | B2 | 12/2003 | Ju et al. |
| 6,858,393 | B1 * | 2/2005 | Anderson et al. ............ 435/6 |
| 7,074,597 | B2 | 7/2006 | Ju |
| 7,329,496 | B2 | 2/2008 | Dower et al. |
| 7,345,159 | B2 | 3/2008 | Ju |
| 7,393,533 | B1 | 7/2008 | Crotty et al. |
| 7,622,279 | B2 | 11/2009 | Ju |
| 7,635,578 | B2 | 12/2009 | Ju et al. |
| 7,713,698 | B2 | 5/2010 | Ju et al. |
| 7,785,790 | B1 | 8/2010 | Church et al. |
| 7,790,869 | B2 | 9/2010 | Ju et al. |
| 7,883,869 | B2 | 2/2011 | Ju et al. |
| 7,982,029 | B2 | 7/2011 | Ju et al. |
| 8,088,575 | B2 | 1/2012 | Ju et al. |
| 8,298,792 | B2 | 10/2012 | Ju et al. |
| 2002/0102586 | A1 | 8/2002 | Ju et al. |
| 2003/0027140 | A1 | 2/2003 | Ju et al. |
| 2004/0185466 | A1 | 9/2004 | Ju et al. |
| 2005/0032081 | A1 | 2/2005 | Ju et al. |
| 2006/0057565 | A1 | 3/2006 | Ju et al. |
| 2006/0240439 | A1 | 10/2006 | Smith et al. |
| 2006/0252038 | A1 | 11/2006 | Ju |
| 2007/0275387 | A1 | 11/2007 | Ju |
| 2008/0131895 | A1 | 6/2008 | Ju et al. |
| 2008/0199868 | A1 | 8/2008 | Ju et al. |
| 2008/0319179 | A1 | 12/2008 | Ju et al. |
| 2009/0088332 | A1 | 4/2009 | Ju et al. |
| 2009/0298072 | A1 | 12/2009 | Ju et al. |
| 2009/0325154 | A1 | 12/2009 | Ju et al. |
| 2010/0323350 | A1 | 12/2010 | Gordon et al. |
| 2011/0014611 | A1 | 1/2011 | Ju et al. |
| 2011/0039259 | A1 | 2/2011 | Ju et al. |

FOREIGN PATENT DOCUMENTS

| | | |
|---|---|---|
| GB | 2446084 B | 3/2011 |
| WO | WO 91/06678 | 5/1991 |
| WO | WO 93/05183 | 3/1993 |
| WO | WO 00/53812 | 9/2000 |
| WO | WO 02/22883 | 3/2002 |
| WO | WO 02/29003 | 4/2002 |
| WO | WO 02/079519 | 10/2002 |
| WO | WO 2004/007773 | 1/2004 |
| WO | WO 2004/055160 | 1/2004 |
| WO | WO 2005/084367 | 9/2005 |
| WO | WO 2007/002204 | 1/2007 |
| WO | WO 2007/053702 | 5/2007 |
| WO | WO 2007/053719 | 5/2007 |
| WO | WO 2007/062105 | 5/2007 |
| WO | WO 2008/069973 | 6/2008 |
| WO | WO 2009/051807 A1 | 4/2009 |

OTHER PUBLICATIONS

Written Opinion issued by the International Searching Authority (ISA/US) on Feb. 6, 2008 in connection with International Application No. PCT/US2006/042739.

Ruparel et al. Design and synthesis of a 3'-O-allyl photocleavable fluorescent nucleotide as a reversible terminator for DNA sequencing by synthesis. PNAS. Apr. 26, 2005, vol. 102, No. 17, pp. 5932-5937.

Ju J., et al. (1996) Cassette labeling for facile construction of energy transfer fluorescent primers. Nuc. Acids Res. 24 (6) : 1144-1148.

Ju J., et al. (1996) Energy transfer primers: A new fluorescence labeling paradigm for DNA sequencing and analysis. Nature Medicine 2: 246-249.

Ju J., et al. (1995) Fluorescence energy transfer dye labeled primers for DNA sequencing and analysis. Proc. Natl. Acad. Sci. USA 92: 4347-4351.

Ju J., et al. (2006) Four color DNA sequencing by synthesis using cleavable fluorescent nucleotide reversible terminators. Proc Natl Acad Sci USA 103: 19635 40.

Notification Concerning Transmittal of International Preliminary Report on Patentability issued Mar. 26, 2009 in connection with International Application No. PCT/US06/042739.

Collin, F. S. et al. A vision for the future of genomics research. Nature. Apr. 24, 2003;422(6934):835-47.

Meng, Q. et al. Design and synthesis of a photocleavable fluorescent nucleotide 3'-O-allyl-dGTP-PC-Bodipy-FL-510 as a reversible terminator for DNA sequencing by synthesis. J Org Chem. Apr. 14, 2006;71(8):3248-52.

Mitra, R. D. et al. Fluorescent in situ sequencing on polymerase colonies. Anal Biochem. Sep. 1, 2003;320(1):55-65.

Pleasants, J.C., et al. A comparative study of the kinetics of selenol/diselenide and thiol/disulfide exchange reactions. *J. Am. Chem. Soc.*, 1989, 111 (17), pp. 6553-6558.

Huyghues-Despointes, B. M. et al. Stabilities of disulfide bond intermediates in the folding of apamin. Biochemistry. Feb. 11, 1992;31(5):1476-83.

Ruparel, H. et al. Design and synthesis of a 3'-O-allyl photocleavable fluorescent nucleotide as a reversible terminator for DNA sequencing by synthesis. Proc Natl Acad Sci U S A. Apr. 26, 2005;102(17):5932-7.

Kang, J. H. et al. Conformationally constrained analogues of diacylglycerol. 24. Asymmetric synthesis of a chiral (R)-DAG-lactone template as a versatile precursor for highly functionalized DAG-lactones. Org Lett. Jul. 8, 2004;6(14):2413-6.

Honma, M., et al. Asymmetric catalysis on the intramolecular cyclopropanation of alpha-diazo-beta-keto sulfones. J Am Chem Soc. Mar. 12, 2003;125(10):2860-1.

Soli, E.D., et al. Azide and Cyanide Displacements via Hypervalent Silicate Intermediates. J Org Chem. Apr. 30, 1999;64(9):3171-3177.

Jacobson, M. A., Generation of 1-azapentadienyl anion from N-(tert-butyldimethylsilyl)-3-buten-1-amine. J Org Chem. May 31, 2002;67(11):3915-8.

Notice of Allowance issued Feb. 24, 2009 in connection with U.S. Appl. No. 11/894,690.

Notice of Allowance issued Mar. 23, 2009 in connection with U.S. Appl. No. 11/894,808.

U.S. Appl. No. 12/084,338, filed Apr. 28, 2008.

U.S. Appl. No. 11/922,385, filed Dec. 14, 2007.

U.S. Appl. No. 12/308,091, filed Dec. 4, 2008.

Communication Pursuant to Article 94(3) EPC issued Apr. 30, 2009 in connection with counterpart European Patent Application No. 07004522.4.

Mathews, Christopher K. and Van Holde, K.E. (1985) "Chemical Synthesis of Oligonucleotides," Biochemistry, $2^{nd}$ Edition, pp. 127-128.

Katherine J. Gibson and Stephen J. Benkovic (1987) "Synthesis and application of derivatizable oligonucleotides," Nucleic Acids Research, vol. 15, No. 16, pp. 6455-6467.

Tatyana S. Godovikova et al. (1999) "5-[3-(E)-(4-Azido-2,3,5,6-tetrafluorobenzamido)propenyl-1]-2'deoxyuridine-5'-triphosphate Substitutes for Thymidine-5' triphosphate in the Polymerase Chain Reaction," Bioconjugate Chem., vol. 10, pp. 529-537.

Amy L. Kimzey and William S. Dynan (1998) "Specific Regions of Contact between Human T-cell Leukemia Virus Type I Tax Protein and DNA Identified by Photocross-linking," The Journal of Biological Chemistry, vol. 273, No. 22, pp. 13768-13775.

Examination Report Under Section 18(3) issued Jan. 28, 2010 in connection with United Kingdom Patent Application No. GB0808033.5.

Examination Report Under Section 18(3) issued Oct. 4, 2010 in connection with United Kingdom Patent Application No. GB0808033.5.

Examination Report Under Section 18(3) issued Jan. 7, 2011 in connection with United Kingdom Patent Application No. GB0808033.5.

(56) References Cited

OTHER PUBLICATIONS

Examination Report Under Section 18(3) issued Jan. 28, 2010 in connection with United Kingdom Patent Application No. GB0808034.3.
Examination Report Under Section 18(3) issued Oct. 4, 2010 in connection with United Kingdom Patent Application No. GB0808034.3; and.
Examination Report Under Section 18(3) issued Jan. 7, 2011 in connection with United Kingdom Patent Application No. GB0808034.3.
Exhibit 2105, filed Dec. 15, 2013 in connection with IPR2012-00006, IPR2012-00007, and IPR2013-00011: Columbia's Demonstratives Under 42.70(b) for Dec. 17, 2013 Oral Hearing.
Exhibit 1057, filed Dec. 16, 2013 in connection with IPR2012-00006, IPR2012-00007, and IPR2013-00011: Illumina's Invalidity Demonstratives for Final Hearing Dec. 17, 2013.
Exhibit 1021, filed Dec. 23, 2013 in connection with IPR2013-00128: Excerpts from Protective Groups in Organic Synthesis (Theodora W. Greene & Peter G. M. Wuts eds., John Wiley & Sons, Inc. 3rd ed. 1999) (1991).
Exhibit 1022, filed Dec. 23, 2013 in connection with IPR2013-00128: Signed Deposition Transcript of Dr. Bruce Branchaud on Oct. 3, 2013, plus errata.
Dec. 30, 2013 Illumina Motion to Amend Under 37 C.F.R. §42.121 in connection with IPR2013-00266.
Exhibits 2004, 2005, and 2028, filed Dec. 30, 2013 in connection with IPR2013-00266: Floyd Romesburg Declaration, CV, and List of Documents Considered by Romesburg.
Exhibit 2006, filed Dec. 30, 2013 in connection with IPR2013-00266: U.S. Appl. No. 12/804,025 application as filed on Jul. 13, 2010 by Balasubramanian et al. [WO 03/048387].
Exhibit 2007, filed Dec. 30, 2013 in connection with IPR2013-00266: U.S. Appl. No. 10/227,131—Barnes et al., filed Aug. 23, 2002.
Exhibit 2008, filed Dec. 30, 2013 in connection with IPR2013-00266: Maxam & Gilbert, PNAS 74:560-564 (Feb. 1977).
Exhibit 2009, filed Dec. 30, 2013 in connection with IPR2013-00266: Sanger et al., DNA Sequencing, PNAS 74:5463-5467 (1977).
Exhibit 2010, filed Dec. 30, 2013 in connection with IPR2013-00266: U.S. Pat. 5,302,509, issued Apr. 12, 1994 to Cheeseman.
Exhibit 2011, filed Dec. 30, 2013 in connection with IPR2013-00266: Metzker et al., Nucleic Acids Research, 22:4259-4267 (1994).
Exhibit 2012, filed Dec. 30, 2013 in connection with IPR2013-00266: Welch and Burgess, Nucleosides & Nucleotides, 18:197-201 (1999).
Exhibit 2013, filed Dec. 30, 2013 in connection with IPR2013-00266: Bruce P. Branchaud, Ph.D., Jun. 4, 2013 Declaration in IPR2013-00324.
Exhibit 2014, filed Dec. 30, 2013 in connection with IPR2013-00266: U.S. Pat. 5,047,519, issued Sep. 10, 1991 to Hobbs.
Exhibit 2015, filed Dec. 30, 2013 in connection with IPR2013-00266: U.S. Pat. 5,242,796, issued Sep. 7, 1993 to Prober.
Exhibit 2016, filed Dec. 30, 2013 in connection with IPR2013-00266: Ruby et al., Methods in Enzymology, 181:97-121 (1990).
Exhibit 2017, filed Dec. 30, 2013 in connection with IPR2013-00266: PCT International Publication No. Wo 96/27025, published Sep. 6, 1996 to Rabini.
Exhibit 2018, filed Dec. 30, 2013 in connection with IPR2013-00266: PCT International Publication No. Wo 89/10977, published Nov. 16, 1989 to Southern.
Exhibit 2019, filed Dec. 30, 2013 in connection with IPR2013-00266: U.S. Pat. 4,772,691, issued Sep. 20, 1998 to Herman.
Exhibit 2020, filed Dec. 30, 2013 in connection with IPR2013-00266: PCT International Publication No. Wo 99/49082, published Sep. 30, 1999 to Short.
Exhibit 2021, filed Dec. 30, 2013 in connection with IPR2013-00266: Bystrom, Branchaud et al., Bioorganic & Medicinal Chemistry Letters, 7:2613-2616 (1997).
Exhibit 2022, filed Dec. 30, 2013 in connection with IPR2013-00266: pp. from Handbook of Reagents for Organic Synthesis: Reagents for Silicon-Mediated Organic Synthesis (Philip L. Fuchs, ed.) (2011).
Exhibit 2023, filed Dec. 30, 2013 in connection with IPR2013-00266: Eric Vermaas Declaration—Redacted version.
Exhibit 2024, filed Dec. 30, 2013 in connection with IPR2013-00266: Excerpts from 2013-10-03 Bruce Branchaud Deposition Transcript in IPR2013-00128.
Exhibit 2025, filed Dec. 30, 2013 in connection with IPR2013-00266: U.S. Pat. 6,001,566, issued Dec. 14, 1999 to Canard.
Exhibit 2026, filed Dec. 30, 2013 in connection with IPR2013-00266: Prober et al., Science 238:336-341 (1987).
Exhibit 2027, filed Dec. 30, 2013 in connection with IPR2013-00266: Ceq 2000 Dna Analysis System User's Guide, Beckman Coulter (Jun. 2000).
Nov. 21, 2013 Decision Denying Institution of Inter Partes Review in connection with IPR2013-00324.
Li et al. (2003) "A Photocleavable Fluorescent Nucleotide for DNA Sequencing and Analysis," PNAS 100(2):414-419.
Seo et al. (2004) "Photocleavable Fluorescent Nucleotides for DNA Sequencing on a Chip Constructed by Site-Specific Coupling Chemistry," PNAS 101(15):5488-5493.
Seo et al. (2005) "Four-Color DNA Sequencing by Synthesis on a Chip Using Photocleavable Fluorescent. Nucleotides," PNAS 102(17):5926-5931.
Office Action issued Oct. 14, 2010 in connection with U.S. Appl. No. 12/084,338.
Notice of Allowance issued Mar. 1, 2011 in connection with U.S. Appl. No. 12/084,338.
Issue Notification issued Jun. 29, 2011 in connection with U.S. Appl. No. 12/084,338.
International Search Report issued Nov. 23, 2007 in connection with international Application No. PCT/US06/42698.
Written Opinion issued Nov. 23, 2007 in connection with International Application No. PCT/US06/42698.
International Preliminary Report on Patentability (Including Written Opinion of the International Searching Authority) issued May 15, 2008 in connection with PCT/US2006/042698.
International Search Report issued Feb. 6, 2008 in connection with international Application No. PCT/US06/42739.
Written Opinion issued Feb. 6, 2003 in connection with International Application No. PCT/US06/42739.
International Preliminary Report on Patentability issued Mar. 17, 2008 in connection with International Application No. PCT/US06/42739.
Sep. 16, 2012 Petition for Inter Partes Review of U.S. Patent No. 7,713,698, issued May 11, 2010.
Sep. 16, 2012 Motion to Waive Page Limit and Proposed Petition in connection with Petition for Inter Partes Review of U.S. Patent No. 7,713,698, issued May 11, 2010.
Dec. 20, 2012 Preliminary Response under 37 C.F.R. 42.107 in connection with IPR2012-00006.
Mar. 12, 2013 Decision on Petition for Inter Partes Review in connection with IPR2012-00006.
Mar. 26, 2013 Request for Reconsideration in connection with IPR2012-00006.
Apr. 26, 2013 Opposition to Request for Reconsideration (Rehearing) Under 37 C.F.R. 42.71.(C) in connection with IPR-2012-00006.
May 10, 2013 Decision on Request for Rehearing in connection with IPR2012-00006.
Aug. 30, 2013 Substitute Patent Owner Response Under 37 C.F.R. 42.120 in connection with IPR2012-00006.
Aug. 30, 2013 Substitute Patent Owner Motion to Amend Under 37 C.F.R. 42.121 in connection with IPR2012-00006.
Sep. 27, 2013 Petitioner Opposition to Motion to Amend in connection with IPR2012-00006.
Sep. 27, 2013 Petitioner Reply to Response to Petition in connection with IPR2012-00006.
Nov. 18, 2013 Substitute Patent Owner Reply on Motion to Amend in connection with IPR2012-00006.
Exhibit 1001, filed Sep. 16, 2012 in connection with IPR2012-00006: U.S. Patent No. 7,713,698, issued May 11, 2010 to Ju et al.

(56) References Cited

OTHER PUBLICATIONS

Exhibit 1002, filed Sep. 16, 2012 in connection with IPR2012-00006: PCT International Application No. PCT/US90/06678 filed Oct. 26, 1990, published on May 16, 1991 as Publication No. WO 91/06678 to SRI INTERNATIONAL.
Exhibit 1003, filed Sep. 16, 2012 in connection with IPR2012-00006: Prober et al. (1987), "A System for Rapid DNA Sequencing with Fluorescent Chain-Terminating Dideoxynucleotides", Science vol. 238, Oct. 16, 1987, pp. 336-341.
Exhibit 1004, filed Sep. 16, 2012 in connection with IPR2012-00006: U.S. Patent No. 5,242,796 issued Sep. 7, 1993 to Prober et al.
Exhibit 1005, filed Sep. 16, 2012 in connection with IPR2012-00006: U.S. Patent No. 5,547,839 issued Aug. 20, 1996 to Dower et al.
Exhibit 1006, filed Sep. 16, 2012 in connection with IPR2012-00006: PCT International Application No. PCT/US96/02342 filed Feb. 21, 1996, published on Sep. 6, 1996 as Publication No. WO 96/27025 to Ely Rabani.
Exhibit 1007, filed Sep. 16, 2012 in connection with IPR2012-00006: PCT International Application No. PCT/GB00/00873 filed Mar. 10, 2000, published on Sep. 14, 2000 as Publication No. WO 00/53805 to ASM Scientific, Inc.
Exhibit 1008, filed Sep. 16, 2012 in connection with IPR2012-00006: U.S. Patent No. 7,270,951 issued Sep. 18, 2007 to Stemple et al.
Exhibit 1009, filed Sep. 16, 2012 in connection with IPR2012-00006: U.S. Application for a Method for Direct Nucleic Acid Sequencing; U.S. Appl. No. 09/266,187 filed Mar. 10, 1999.
Exhibits 1010-1012, filed Sep. 16, 2012 in connection with IPR2012-00006: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Sep. 16, 2012 in connection with IPR2012-00006: U.S. Patent No. 5,047,519 issued Sep. 10, 1991 to Hobbs, Jr. et al.
Exhibit 1014, filed Sep. 16, 2012 in connection with IPR2012-00006: U.S. Patent No. 4,804,748 issued Feb. 14, 1989 to Seela.
Exhibit 1015, filed Sep. 16, 2012 in connection with IPR2012-00006: U.S. Patent No. 5,844,106 issued Dec. 1, 1998 to Seela et al.
Exhibit 1016, filed Sep. 16, 2012 in connection with IPR2012-00006: PCT International Application No. PCT/US89/02170, filed May 18, 1989, published on Nov. 30, 1989 as Publication No. WO 89/11548 to Cetus Corporation.
Exhibit 1017, filed Sep. 16, 2012 in connection with IPR2012-00006: U.S. Patent No. 7,037,687 issued May 2, 2006 to Williams et al.
Exhibit 1018, filed Sep. 16, 2012 in connection with IPR2012-00006: U.S. Patent No. 6,255,083 issued Jul. 3, 2001 to Williams.
Exhibit 1019, filed Sep. 16, 2012 in connection with IPR2012-00006: U.S. Patent No. 6,001,566 issued Dec. 14, 1999 to Canard et al.
Exhibit 1020, filed Sep. 16, 2012 in connection with IPR2012-00006: PCT International Application No. PCT/GB93/00848, filed Apr. 22, 1993, published on Oct. 28, 1993 as Publication No. Wo 93/21340 to Medical Research Council.
Exhibit 1021, filed Sep. 16, 2012 in connection with IPR2012-00006: Sep. 15, 2012 Declaration of George Weinstock Under Rule 37 C.F.R. §1.132.
Exhibit 1022, filed Sep. 16, 2012 in connection with IPR2012-00006: Excerpts of File History of U.S. Patent No. 7,713,698.
Exhibit 1025, filed Apr. 30, 2013 in connection with IPR2012-00006: Columbia's Amended Complaint from the Trustees of Columbia University in the City of New York v. Illumina, Inc., D. Del C.A. No. 12-376 (GMS), filed Apr. 11, 2012.
Exhibit 1026, filed Apr. 30, 2013 in connection with IPR2012-00006: Illumina's Answer to Amended Complaint from the Trustees of Columbia University in the City of New York v. Illumina, Inc., D. Del C.A. No. 12-376 (GMS), filed Dec. 21, 2012.
Exhibit 1029, filed Jun. 18, 2013 in connection with IPR2012-00006: U.S. Patent No. 4,772,691, issued Sep. 20, 1988 to Herman.
Exhibit 1030, filed Jun. 18, 2013 in connection with IPR2012-00006: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2012-00006: PCT International Publication No. WO 99/49082, published Sep. 30, 1999 to Invitrogen Corporation.
Exhibit 1032, filed Jun. 18, 2013 in connection with IPR2012-00006: U.S. Patent No. 5,449,767, issued Sep. 12, 1995 to Ward et al.
Exhibit 1033, filed Jun. 18, 2013 in connection with IPR2012-00006: U.S. Patent No. 5,948,648, issued Sep. 7, 1999 to Khan et al.
Exhibit 1034, filed Jun. 18, 2013 in connection with IPR2012-00006: Jun. 8, 2013 Videotaped Deposition Transcript of George M. Weinstock, Ph.D.
Exhibit 1036, filed Sep. 27, 2013 in connection with IPR2012-00006: "Next Generation Genomics: World Map of High-throughput Sequencers," Sep. 1, 2013.
Exhibit 1037, filed Sep. 27, 2013 in connection with IPR2012-00006: GB Application No. 2001 0029012, filed Dec. 4, 2001 by Balasubramanian et al.
Exhibit 1039, filed Sep. 27, 2013 in connection with IPR2012-00006: Videotaped Deposition Transcript of Dr. Xiaohai Liu, Mar. 20, 2013.
Exhibit 1040, filed Sep. 27, 2013 in connection with IPR2012-00006: Excerpt from videotaped Deposition Transcript of George M. Weinstock, Ph.D., Jun. 8, 2013.
Exhibit 1041, filed Sep. 27, 2013 in connection with IPR2012-00006: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2012-00006: Ramzaeva et al., "123. 7-Deazaguanine Dna: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00006: Ramzaeva et al., "88. 7-Substituted 7-Deaza- 2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00006: Seela et al., "Duplex Stability of Oligonucleotides Containing 7-Substituted 7-Deaza- and 8-Aza-7-Deazapurine Nucleosides," Nucleosides & Nucleotides, 16(7-9), pp. 963-966, 1997.
Exhibit 1045, filed Sep. 27, 2013 in connection with IPR2012-00006: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2012-00006: U.S. Patent No. 5,151,507, issued Sep. 29, 1992 to Hobbs, Jr. et al.
Exhibit 1047, filed Sep. 27, 2013 in connection with IPR2012-00006: U.S. Patent No. 7,078,499, issued Jul. 18, 2006 to Odedra et al.
Exhibit 1048, filed Sep. 27, 2013 in connection with IPR2012-00006: GB Application No. 2000 0013276, filed Jun. 1, 2000 by Odedra et al.
Exhibit 1049, filed Sep. 27, 2013 in connection with IPR2012-00006: Jan. 28, 2013 Declaration of Dr. Bruce P. Branchaud in Support of Petition for Inter Partes Review of U.S. Patent No. 7,057,026.
Exhibit 1050, filed Sep. 27, 2013 in connection with IPR2012-00006: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00006: http://www.answers.com/topic/incubate, Accessed Sep. 27, 2013.
Exhibit 1052, filed Sep. 27, 2013 in connection with IPR2012-00006: http://en.wikipedia.org/wiki/Fluorenylmethyloxycarbonyl_chloride, Accessed Sep. 27, 2013.
Exhibit 1053, filed Sep. 27, 2013 in connection with IPR2012-00006: Sep. 27, 2013 Declaration of Kevin Burgess.
Exhibit 1054, filed Sep. 27, 2013 in connection with IPR2012-00006: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Dec. 20, 2012 in connection with IPR2012-00006: U.S. Patent No. 5,383,858, issued Jan. 24, 1995 to Reilly et al.
Exhibit 2006, filed Apr. 26, 2013 in connection with IPR2012-00006: Dower patent with highlights.
Exhibit 2010, filed Jun. 24, 2013 in connection with IPR2012-00006: U.S. Pat. No. 8,088,575 (filed Jul. 19, 2010, issued Jan. 3, 2012) (Exhibit 1001 in IPR2013-00011).

(56) References Cited

OTHER PUBLICATIONS

Exhibit 2011, filed Jun. 24, 2013 in connection with IPR2012-00006: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2012-00006: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2012-00006: Oct. 2, 2012 Declaration of George Weinstock Under 37 Cfr 1.132 (Exhibit 1021 in IPR2013-00011).
Exhibit 2014, filed Jun. 24, 2013 in connection with IPR2012-00006: Petition for Inter Partes Review of U.S. Pat. No. 8,088,575 (Paper 4 in IPR2013-00011).
Exhibit 2015, filed Jun. 24, 2013 in connection with IPR2012-00006: Metzker et al. (1994) Termination of Dna synthesis by novel 3'-modified-deoxyribonucleoside 5'-triphosphates. Nucleic Acids Res. 22:4259-4267.
Exhibit 2016, filed Jun. 24, 2013 in connection with IPR2012-00006: Wu et al. (2007) Termination of Dna synthesis by N6- alkylated, not 3'-0-alkylated, photocleavable 2'- deoxyadenosine triphosphates. Nucleic Acids Res. 35:6339-6349.
Exhibit 2017, filed Jun. 24, 2013 in connection with IPR2012-00006: Sep. 15, 2012 Declaration of George Weinstock Under 37 Cfr 1.132 (Exhibit 1021 in TER2012-00007).
Exhibit 2018, filed Jun. 24, 2013 in connection with IPR2012-00006: Sep. 15, 2012 Declaration of George Weinstock Under 37 Cfr 1.132 (Exhibit 1021 in IPR2012-00006).
Exhibit 2019, filed Jun. 24, 2013 in connection with IPR2012-00006: Definition of "DNA microarray." http://en/wikipedia.org/wiki/DNA microarray.
Exhibit 2020, filed Jun. 24, 2013 in connection with IPR2012-00006: Brettin et al. (2005) Expression capable library for studies of Neisseria gonorrhoeae, version 1.0 BMC Microbiology. 5:50.
Exhibit 2021, filed Jun. 24, 2013 in connection with IPR2012-00006: George M. Weinstock, Handbook of Molecular Microbial Ecology, vol. 1-Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2012-00006: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2012-00006: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00006: Maxam and Gilbert (1977) A new method for sequencing DNA, Proc. Natl. Acad. Sci. USA. 74:560-564.
Exhibit 2025, filed Jun. 24, 2013 in connection with IPR2012-00006: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00006: Pennisi (2000) DOE Team Sequences Three Chromosomes, Science. 288:417-419.
Exhibit 2027, filed Jun. 24, 2013 in connection with IPR2012-00006: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2012-00006: Hyman (1998) A New Method of Sequencing DNA, Analytical Biochemistry 174:423-436.
Exhibit 2029, filed Jun. 24, 2013 in connection with IPR2012-00006: U.S. Pat. No. 5,302,509 (filed Feb. 27, 1991, issued Apr. 12, 1994).
Exhibit 2030, filed Jun. 24, 2013 in connection with IPR2012-00006: Canard and Sarfati (1994) DNA polymerase fluorescent substrates with reversible 3'-tags, Gene. 1481-6.
Exhibit 2031, filed Jun. 24, 2013 in connection with IPR2012-00006: U.S. Pat. No. 8,399,188 (filed Sep. 4, 2007, issued Mar. 19, 2013).
Exhibit 2032, filed Jun. 24, 2013 in connection with IPR2012-00006: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00006: Jun. 25, 2013 Substitute Declaration of Dr. George L. Trainor [redacted].
Exhibit 2034, filed Jun. 25, 2013 in connection with IPR2012-00006: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00006: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2012-00006: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2012-00006: Oct. 1, 2006 Request for opinion on manuscript by J. Ju et. al., Proceedings of National Academy of Sciences, U.S.A.
Exhibit 2038, filed Jun. 25, 2013 in connection with IPR2012-00006: Correspondence between George Rupp, Chancellor, Columbia University and Richard T. Schlossberg, President, the David and Lucile Packard Foundation (2001).
Exhibit 2039, filed Jun. 25, 2013 in connection with IPR2012-00006: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 25, 2013 in connection with IPR2012-00006: "Chemistry for Next-Generation Sequencing." http://www.illumina.com/technology/sequencing technology.ilmn.
Exhibit 2041, filed Jun. 25, 2013 in connection with IPR2012-00006: Chiang et al. (2010) Mammalian microRNAs: experimental evaluation of novel and previously annotated genes, Genes & Dev. 24:992, 993.
Exhibit 2042, filed Jun. 25, 2013 in connection with IPR2012-00006: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 25, 2013 in connection with IPR2012-00006: Curriculum vitae of Mr. Raymond S. Sims.
Exhibit 2044, filed Jun. 25, 2013 in connection with IPR2012-00006: Prior Testimony of Mr. Raymond S. Sims.
Exhibit 2045, filed Jun. 25, 2013 in connection with IPR2012-00006: Documents reviewed by Mr. Raymond S. Sims in this Proceeding.
Exhibit 2052, filed Jun. 25, 2013 in connection with IPR2012-00006: Gary Schroth Proof of Chiang Paper.
Exhibit 2074, filed Jun. 25, 2013 in connection with IPR2012-00006: Information about Dr. Ju's intellectual property sent to Illumina.
Exhibit 2090, filed Jun. 26, 2013 in connection with IPR2012-00006: IPR Default Protective Order.
Exhibit 2091, filed Jun. 26, 2013 in connection with IPR2012-00006: Declaration of Raymond S. Sims.
Exhibit 2092, filed Oct. 10, 2013 in connection with IPR2012-00006: Rough Transcript of the Sep. 4, 2013 deposition of Dr. George L. Trainor.
Exhibit 2093, filed Oct. 1, 2013 in connection with IPR2012-00006: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00006: Final transcript of the Sep. 4-6, 2013 deposition of Dr. George L. Trainor.
Exhibit 2095, filed Oct. 1, 2013 in connection with IPR2012-00006: Final transcript of the Sep. 3, 2013 deposition of Raymond S. Sims.
Nov. 12, 2013 Petitioner Motion to Exclude Evidence in connection with IPR2012-00006.
Exhibit 1056, filed Nov. 19, 2013 in connection with TPR2012-00006: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in connection with IPR2012-00006.

(56) References Cited

OTHER PUBLICATIONS

Nov. 12, 2013 Patent Owner Motion to Exclude Evidence in connection with IPR2012-00006.
Exhibit 2099, filed Nov. 12, 2013 in connection with IPR2012-00006: Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2012-00006: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2012-00006: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2012-00006: Advanced Sequencing Technology Awards 2004. http://www.genome.gov/12513162 (accessed Oct. 14, 2013).
Exhibit 2103, filed Nov. 12, 2013 in connection with IPR2012-00006: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Sep. 16, 2012 Petition for Inter Partes Review of U.S. Patent No. 7,790,869.
Sep. 17, 2012 Motion to Waive Page Limit and Proposed Petition in connection with Petition for Inter Partes Review of U.S. Patent No. 7,790,869.
Dec. 21, 2012 Preliminary Response under 37 C.F.R. 42.107 in connection with IPR2012-00007.
Mar. 12, 2013 Decision on Petition for Inter Partes Review in connection with IPR2012-00007.
Mar. 26, 2013 Request for Reconsideration in connection with IPR2012-00007.
Mar. 26, 2013 Request for Rehearing under 37 C.F.R. 42.71 of Decision to Institute Inter Partes Review in connection with IPR2012-00007.
Apr. 26, 2013 Opposition to Request for Reconsideration (Rehearing) Under 37 C.F.R. 42.71.(C) in connection with IPR2012-00007.
May 10, 2013 Decision on Request for Rehearing in connection with IPR2012-00007.
Aug. 30, 2013 Substitute Patent Owner Response Under 37 C.F.R. 42.120 in connection with IPR2012-00007.
Aug. 30, 2013 Substitute Patent Owner Motion to Amend Under 37 C.F.R. 42.121 in connection with IPR2012-00007.
Sep. 27, 2013 Petitioner Opposition to Motion to Amend in connection with IPR2012-00007.
Sep. 27, 2013 Petitioner Reply to Response to Petition in connection with IPR2012-00007.
Nov. 18, 2013 Substitute Patent Owner Reply on Motion to Amend in connection with IPR2012-00007.
Exhibit 1001, filed Sep. 16, 2012 in connection with IPR2012-00007: U.S. Patent No. 7,790,869 issued Sep. 7, 2010 to Ju et al.
Exhibit 1002, filed Sep. 16, 2012 in connection with IPR2012-00007: PCT International Application No. PCT/US90/06678 filed Oct. 26, 1990, published on May 16, 1991 as Publication No. WO 91/06678 to SRI International.
Exhibit 1003, filed Sep. 16, 2012 in connection with IPR2012-00007: Prober et al. (1987), "A System for Rapid DNA Sequencing with Fluorescent Chain-Terminating Dideoxynucleotides", *Science* vol. 238, Oct. 16, 1987, pp. 336-341.
Exhibit 1004, filed Sep. 16, 2012 in connection with IPR2012-00007: U.S. Patent No. 5,242,796 issued Sep. 7, 1993 to Prober et al.
Exhibit 1005, filed Sep. 16, 2012 in connection with IPR2012-00007: U.S. Patent No. 5,547,839 issued Aug. 20, 1996 to Dower et al.
Exhibit 1006, filed Sep. 16, 2012 in connection with IPR2012-00007: PCT International Application No. PCT/US96/02342 filed Feb. 21, 1996, published on Sep. 6, 1996 as Publication No. WO 96/27025 to Ely Rabani.
Exhibit 1007, filed Sep. 16, 2012 in connection with IPR2012-00007: PCT International Application No. PCT/GB00/00873 filed Mar. 10, 2000, published on Sep. 14, 2000 as Publication No. WO 00/53805 to ASM Scientific, Inc.
Exhibit 1008, filed Sep. 16, 2012 in connection with IPR2012-00007: U.S. Patent No. 7,270,951 issued Sep. 18, 2007 to Stemple et al.
Exhibit 1009, filed Sep. 16, 2012 in connection with IPR2012-00007: U.S. Application for a Method for Direct Nucleic Acid Sequencing; U.S. Appl. No. 09/266,187 filed Mar. 10, 1999.
Exhibits 1010-1012, filed Sep. 16, 2012 in connection with IPR2012-00007: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Sep. 16, 2012 in connection with IPR2012-00007: U.S. Patent No. 5,047,519 issued Sep. 10, 1991 to Hobbs, Jr. et al.
Exhibit 1014, filed Sep. 16, 2012 in connection with IPR2012-00007: U.S. Patent No. 4,804,748 issued Feb. 14, 1989 to Seela.
Exhibit 1015, filed Sep. 16, 2012 in connection with IPR2012-00007: U.S. Patent No. 5,844,106 issued Dec. 1, 1998 to Seela et al.
Exhibit 1016, filed Sep. 16, 2012 in connection with IPR2012-00007: PCT International Application No. PCT/US89/02170, filed May 18, 1989, published on Nov. 30, 1989 as Publication No. WO 89/11548 to Cetus Corporation.
Exhibit 1017, filed Sep. 16, 2012 in connection with IPR2012-00007: U.S. Patent No. 7,037,687 issued May 2, 2006 to Williams et al.
Exhibit 1018, filed Sep. 16, 2012 in connection with IPR2012-00007: U.S. Patent No. 6,255,083 issued Jul. 3, 2001 to Williams.
Exhibit 1019, filed Sep. 16, 2012 in connection with IPR2012-00007: U.S. Patent No. 6,001,566 issued Dec. 14, 1999 to Canard et al.
Exhibit 1020, filed Sep. 16, 2012 in connection with IPR2012-00007: PCT International Application No. PCT/GB93/00848, filed Apr. 22, 1993, published on Oct. 28, 1993 as Publication No. Wo 93/21340 to Medical Research Council.
Exhibit 1021, filed Sep. 16, 2012 in connection with IPR2012-00007: Sep. 15, 2012 Declaration of George Weinstock Under Rule 37 C.F.R. §1.132.
Exhibit 1022, filed Sep. 16, 2012 in connection with IPR2012-00007: Excerpts of File History of U.S. Patent No. 7,790,869.
Exhibit 1025, filed Apr. 30, 2013 in connection with IPR2012-00007: Columbia's Amended Complaint from the Trustees of Columbia University in the City of New York v. Illumina, Inc., D. Del C.A. No. 12-376 (GMS), filed Apr. 11, 2012.
Exhibit 1026, filed Apr. 30, 2013 in connection with IPR2012-00007: Illumina's Answer to Amended Complaint from the Trustees of Columbia University in the City of New York v. Illumina, Inc., D. Del C.A. No. 12-376 (GMS), filed Dec. 21, 2012.
Exhibit 1029, filed Jun. 18, 2013 in connection with IPR2012-00007: U.S. Patent No. 4,772,691, issued Sep. 20, 1988 to Herman.
Exhibit 1030, filed Jun. 18, 2013 in connection with IPR2012-00007: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2012-00007: PCT International Publication No. WO 99/49082, published Sep. 30, 1999 to Invitrogen Corporation.
Exhibit 1032, filed Jun. 18, 2013 in connection with IPR2012-00007: U.S. Patent No. 5,449,767, issued Sep. 12, 1995 to Ward et al.
Exhibit 1033, filed Jun. 18, 2013 in connection with IPR2012-00007: U.S. Patent No. 5,948,648, issued Sep. 7, 1999 to Khan et al.
Exhibit 1034, filed Jun. 18, 2013 in connection with IPR2012-00007: Jun. 8, 2013 Videotaped Deposition Transcript of George M. Weinstock, Ph.D.
Exhibit 1036, filed Sep. 27, 2013 in connection with IPR2012-00007: "Next Generation Genomics: World Map of High-throughput Sequencers," Sep. 1, 2013.
Exhibit 1037, filed Sep. 27, 2013 in connection with IPR2012-00007: GB Application No. 2001 0029012, filed Dec. 4, 2001 by Balasubramanian et al.

(56) References Cited

OTHER PUBLICATIONS

Exhibit 1039, filed Sep. 27, 2013 in connection with IPR2012-00007: Videotaped Deposition Transcript of Dr. Xiaohai Liu, Mar. 20, 2013.
Exhibit 1040, filed Sep. 27, 2013 in connection with IPR2012-00007: Excerpt from videotaped Deposition Transcript of George M. Weinstock, Ph.D., Jun. 8, 2013.
Exhibit 1041, filed Sep. 27, 2013 in connection with IPR2012-00007: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2012-00007: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00007: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00007: Seela et al., "Duplex Stability of Oligonucleotides Containing 7-Substituted 7-Deaza- and 8-Aza-7-Deazapurine Nucleosides," Nucleosides & Nucleotides, 16(7- 9), pp. 963-966, 1997.
Exhibit 1045, filed Sep. 27, 2013 in connection with IPR2012-00007: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2012-00007: U.S. Patent No. 5,151,507, issued Sep. 29, 1992 to Hobbs, Jr. et al.
Exhibit 1047, filed Sep. 27, 2013 in connection with IPR2012-00007: U.S. Patent No. 7,078,499, issued Jul. 18, 2006 to Odedra et al.
Exhibit 1048, filed Sep. 27, 2013 in connection with IPR2012-00007: GB Application No. 2000 0013276, filed Jun. 1, 2000 by Odedra et al.
Exhibit 1049, filed Sep. 27, 2013 in connection with IPR2012-00007: Jan. 28, 2013 Declaration of Dr. Bruce P. Branchaud in Support of Petition for Inter Partes Review of U.S. Patent No. 7,057,026.
Exhibit 1050, filed Sep. 27, 2013 in connection with IPR2012-00007: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00007: http://www.answers.com/topic/incubate, Accessed Sep. 27, 2013.
Exhibit 1052, filed Sep. 27, 2013 in connection with IPR2012-00007: http://en.wikipedia.org/wiki/Fluorenylmethyloxycarbonyl_chloride, Accessed Sep. 27, 2013.
Exhibit 1053, filed Sep. 27, 2013 in connection with IPR2012-00007: Sep. 27, 2013 Declaration of Kevin Burgess.
Exhibit 1054, filed Sep. 27, 2013 in connection with IPR2012-00007: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Dec. 21, 2012 in connection with IPR2012-00007: Composition of a Nucleotide.
Exhibit 2006, filed Jun. 25, 2013 in connection with IPR2012-00007: Dower patent with highlights.
Exhibit 2010, filed Jun. 24, 2013 in connection with IPR2012-00007: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2012-00007: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2012-00007: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2012-00007: Oct. 2, 2012 Declaration of George Weinstock Under 37 CFR 1.132 (Exhibit 1021 in IPR2013-00011).
Exhibit 2014, filed Jun. 24, 2013 in connection with IPR2012-00007: Petition for Inter Partes Review of U.S. Pat. No. 8,088,575 (Paper 4 in IPR2013-00011).
Exhibit 2015, filed Jun. 24, 2013 in connection with IPR2012-00007: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2012-00007: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2012-00007: Sep. 15, 2012 Declaration of George Weinstock Under 37 CFR 1.132 (Exhibit 1021 in IPR2012-00007).
Exhibit 2018, filed Jun. 24, 2013 in connection with IPR2012-00007: Sep. 15, 2012 Declaration of George Weinstock Under 37 CFR 1.132 (Exhibit 1021 in IPR2012-00006).
Exhibit 2019, filed Jun. 24, 2013 in connection with IPR2012-00007: Definition of "DNA microarray." http://en/wikipedia.org/wiki/DNA_microarray.
Exhibit 2020, filed Jun. 24, 2013 in connection with IPR2012-00007: Brettin et al. (2005) Expression capable library for studies of Neisseria gonorrhoeae, version 1.0 BMC Microbiology. 5:50.
Exhibit 2021, filed Jun. 24, 2013 in connection with IPR2012-00007: George M. Weinstock, Handbook of Molecular Microbial Ecology, vol. 1-Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2012-00007: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2012-00007: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00007: Maxam and Gilbert (1977) A new method for sequencing DNA, Proc. Natl. Acad. Sci. USA. 74:560-564.
Exhibit 2025, filed Jun. 24, 2013 in connection with IPR2012-00007: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00007: Pennisi (2000) DOE Team Sequences Three Chromosomes, Science. 288:417-419.
Exhibit 2027, filed Jun. 24, 2013 in connection with IPR2012-00007: Welch and Burgess (1999) Synthesis of Fluorescent, Photolabile 3'-0-Protected nucleoside Triphosphates for the Base Addition Sequencing Scheme, nucleosides & Nucleotides. 18:197-201.
Exhibit 2028, filed Jun. 24, 2013 in connection with IPR2012-00007: Hyman (1998) A New Method of Sequencing DNA, Analytical Biochemistry 174:423-436.
Exhibit 2029, filed Jun. 24, 2013 in connection with IPR2012-00007: U.S. Pat. No. 5,302,509 (filed Feb. 27, 1991, issued Apr. 12, 1994).
Exhibit 2030, filed Jun. 24, 2013 in connection with IPR2012-00007: Canard and Sarfati (1994) DNA polymerase fluorescent substrates with reversible 3'-tags, Gene. 1481-6.
Exhibit 2031, filed Jun. 24, 2013 in connection with IPR2012-00007: U.S. Pat. No. 8,399,188 (filed Sep. 4, 2007, issued Mar. 19, 2013).
Exhibit 2032, filed Jun. 24, 2013 in connection with IPR2012-00007: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00007: Jun. 25, 2013 Substitute Declaration of Dr. George L. Trainor [redacted].
Exhibit 2034, filed Jun. 25, 2013 in connection with IPR2012-00007: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00007: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2012-00007: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.

(56) References Cited

OTHER PUBLICATIONS

Exhibit 2037, filed Jun. 25, 2013 in connection with IPR2012-00007: Oct. 1, 2006 Request for opinion on manuscript by J. Ju et. al., Proceedings of National Academy of Sciences, U.S.A.
Exhibit 2038, filed Jun. 25, 2013 in connection with IPR2012-00007: Correspondence between George Rupp, Chancellor, Columbia University and Richard T. Schlossberg, President, The David and Lucile Packard Foundation (2001).
Exhibit 2039, filed Jun. 25, 2013 in connection with IPR2012-00007: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 26, 2013 in connection with IPR2012-00007: "Chemistry for Next-Generation Sequencing." http://www.illumina.com/technology/sequencing_technology.ilmn.
Exhibit 2041, filed Jun. 26, 2013 in connection with IPR2012-00007: Chiang et al. (2010) Mammalian microRNAs: experimental evaluation of novel and previously annotated genes, Genes & Dev. 24:992, 993.
Exhibit 2042, filed Jun. 26, 2013 in connection with IPR2012-00007: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 26, 2013 in connection with IPR2012-00007: Curriculum vitae of Mr. Raymond S. Sims.
Exhibit 2044, filed Jun. 26, 2013 in connection with IPR2012-00007: Prior Testimony of Mr. Raymond S. Sims.
Exhibit 2045, filed Jun. 26, 2013 in connection with IPR2012-00007: Documents reviewed by Mr. Raymond S. Sims in this Proceeding.
Exhibit 2052, filed Jun. 26, 2013 in connection with IPR2012-00007: Gary Schroth Proof of Chiang Paper.
Exhibit 2074, filed Jun. 26, 2013 in connection with IPR2012-00007: Information about Dr. Ju's intellectual property sent to Illumina.
Exhibit 2090, filed Jun. 26, 2013 in connection with IPR2012-00007: IPR Default Protective Order.
Exhibit 2091, filed Jun. 26, 2013 in connection with IPR2012-00007: Declaration of Raymond S. Sims.
Exhibit 2092, filed Oct. 1, 2013 in connection with IPR2012-00007: Rough transcript of the Sep. 4, 2013 deposition of Dr. George L. Trainor.
Exhibit 2093, filed Oct. 1, 2013 in connection with IPR2012-00007: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00007: Final transcript of the Sep. 4-6, 2013 deposition of Dr. George L. Trainor.
Exhibit 2095, filed Oct. 1, 2013 in connection with IPR2012-00007: Final transcript of the Sep. 3, 2013 deposition of Raymond S. Sims.
Nov. 12, 2013 Petitioner Motion to Exclude Evidence in connection with IPR2012-00007.
Exhibit 1056, filed Nov. 19, 2013 in connection with TPR2012-00007: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in Connection with IPR-2012-00007.
Nov. 12, 2013 Patent Owner Motion to Exclude Evidence in connection with IPR2012-00007.
Exhibit 2099, filed Nov. 12, 2013 in connection with IPR2012-00007: Welch, M., et al (2005) Corrigenda to Syntheses of Nucleosides Designed for Combinatorial DNA Sequencing Chem. Eur. J., 1999, 951-960. Published in Chem. Eur. J, 2005, 11, 7136-7145.
Exhibit 2100, filed Nov. 12, 2013 in connection with IPR2012-00007: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2012-00007: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2012-00007: Advanced Sequencing Technology Awards 2004. http://www.genome.gov/12513162 (accessed Oct. 14, 2013).
Exhibit 2103, filed Nov. 12, 2013 in connection with IPR2012-00007: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Oct. 3, 2012 Petition for Inter Partes Review of U.S. Patent No. 8,088,575.
Oct. 3, 2012 Motion to Waive Page Limit and Proposed Petition in connection with Petition for Inter Partes Review of U.S. Patent No. 8,088,575.
Jan. 7, 2013 Preliminary Response under 37 C.F.R. 42.107 in connection with IPR2013-00011.
Mar. 12, 2013 Decision on Petition for Inter Partes Review in connection with IPR2013-00011.
Mar. 26, 2013 Request for Reconsideration in connection with IPR2013-00011.
Mar. 26, 2013 Request for Rehearing under 37 C.F.R. 42.71 of Decision to Institute Inter Partes Review in connection with IPR2013-00011.
Apr. 26, 2013 Opposition to Request for Reconsideration (Rehearing) Under 37 C.F.R. 42.71.(C) in connection with IPR2013-00011.
May 10, 2013 Decision on Request for Rehearing in connection with IPR2013-00011.
Jun. 25, 2013 Motion to Amend Under 37 C.F.R. 42.121 in connection with IPR2013-00011.
Aug. 30, 2013 Substitute Patent Owner Response Under 37 C.F.R. 42.120 in connection with IPR2013-00011.
Sep. 27, 2013 Petitioner Opposition to Motion to Amend in connection with IPR2013-00011.
Sep. 27, 2013 Petitioner Reply to Response to Petition in connection with IPR2013-00011.
Nov. 18, 2013 Substitute Patent Owner Reply on Motion to Amend in connection with IPR2013-00011.
Exhibit 1001, filed Oct. 3, 2012 in connection with IPR2013-00011: U.S. Patent No. 8,088,575 issued Jan. 3, 2012 to Ju et al.
Exhibit 1002, filed Oct. 3, 2012 in connection with IPR2013-00011: PCT International Application No. PCT/US90/06678 filed Oct. 26, 1990, published on May 16, 1991 as Publication No. WO 91/06678 to SRI International.
Exhibit 1003, filed Oct. 3, 2012 in connection with IPR2013-00011: Prober et al. (1987), "A System for Rapid DNA Sequencing with Fluorescent Chain-Terminating Dideoxynucleotides", *Science* vol. 238, Oct. 16, 1987, pp. 336-341.
Exhibit 1004, filed Oct. 3, 2012 in connection with IPR2013-00011: U.S. Patent No. 5,242,796 issued Sep. 7, 1993 to Prober et al.
Exhibit 1005, filed Oct. 3, 2012 in connection with IPR2013-00011: U.S. Patent No. 5,547,839 issued Aug. 20, 1996 to Dower et al.
Exhibit 1006, filed Oct. 3, 2012 in connection with IPR2013-00011: PCT International Application No. PCT/US96/02342 filed Feb. 21, 1996, published on Sep. 6, 1996 as Publication No. WO 96/27025 to Ely Rabani.
Exhibit 1007, filed Oct. 3, 2012 in connection with IPR2013-00011: PCT International Application No. PCT/GB00/00873 filed Mar. 10, 2000, published on Sep. 14, 2000 as Publication No. WO 00/53805 to ASM Scientific, Inc.
Exhibit 1008, filed Oct. 3, 2012 in connection with IPR2013-00011: U.S. Patent No. 7,270,951 issued Sep. 18, 2007 to Stemple et al.
Exhibit 1009, filed Oct. 3, 2012 in connection with IPR2013-00011: U.S. Application for A Method for Direct Nucleic Acid Sequencing; U.S. Appl. No. 09/266,187, filed Mar. 10, 1999.
Exhibits 1010-1012, filed Oct. 3, 2012 in connection with IPR2013-00011: PCT International Application No. PCT/JP97/00239, filed

(56) References Cited

OTHER PUBLICATIONS

Jan. 31, 1997, published on Aug. 6, 1998 as Publication No. WO 98/33939 to Hitachi, Ltd. with certified English translation, and Translation Affidavit.
Exhibit 1013, filed Oct. 3, 2012 in connection with IPR2013-00011: U.S. Patent No. 5,047,519 issued Sep. 10, 1991 to Hobbs, Jr. et al.
Exhibit 1014, filed Oct. 3, 2012 in connection with IPR2013-00011: U.S. Patent No. 4,804,748 issued Feb. 14, 1989 to Seela.
Exhibit 1015, filed Oct. 3, 2012 in connection with IPR2013-00011: U.S. Patent No. 5,844,106 issued Dec. 1, 1998 to Seela et al.
Exhibit 1016, filed Oct. 3, 2012 in connection with IPR2013-00011: PCT International Application No. PCT/US89/02170, filed May 18, 1989, published on Nov. 30, 1989 as Publication No. WO 89/11548 to Cetus Corporation.
Exhibit 1017, filed Oct. 3, 2012 in connection with IPR2013-00011: U.S. Patent No. 7,037,687 issued May 2, 2006 to Williams et al.
Exhibit 1018, filed Oct. 3, 2012 in connection with IPR2013-00011: U.S. Patent No. 6,255,083 issued Jul. 3, 2001 to Williams.
Exhibit 1019, filed Oct. 3, 2012 in connection with IPR2013-00011: U.S. Patent No. 6,001,566 issued Dec. 14, 1999 to Canard et al.
Exhibit 1020, filed Oct. 3, 2012 in connection with IPR2013-00011: PCT International Application No. PCT/GB93/00848, filed Apr. 22, 1993, published on Oct. 28, 1993 as Publication No. WO 93/21340 to Medical Research Council.
Exhibit 1021, filed Oct. 3, 2012 in connection with IPR2013-00011: Oct. 3, 2012 Declaration of George Weinstock Under Rule 37 C.F.R. §1.132.
Exhibit 1022, filed Oct. 3, 2012 in connection with IPR2013-00011: Excerpts of File History of U.S. Patent No. 8,088,575.
Exhibit 1025, filed Apr. 30, 2013 in connection with IPR2013-00011: Columbia's Amended Complaint from *The Trustees of Columbia University in the City of New York v. Illumina, Inc.*, D. Del C.A. No. 12-376 (GMS), filed Apr. 11, 2012.
Exhibit 1026, filed Apr. 30, 2013 in connection with IPR2013-00011: Illumina's Answer to Amended Complaint from *The Trustees of Columbia University in the City of New York v. Illumina, Inc.*, D. Del C.A. No. 12-376 (GMS), filed Dec. 21, 2012.
Exhibit 1029, filed Jun. 18, 2013 in connection with IPR2013-00011: U.S. Patent No. 4,772,691, issued Sep. 20, 1988 to Herman.
Exhibit 1030, filed Jun. 18, 2013 in connection with IPR2013-00011: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2013-00011: PCT International Publication No. WO 99/49082, published Sep. 30, 1999 to Invitrogen Corporation.
Exhibit 1032, filed Jun. 18, 2013 in connection with IPR2013-00011: U.S. Patent No. 5,449,767, issued Sep. 12, 1995 to Ward et al.
Exhibit 1033, filed Jun. 18, 2013 in connection with IPR2013-00011: U.S. Patent No. 5,948,648, issued Sep. 7, 1999 to Khan et al.
Exhibit 1034, filed Jun. 18, 2013 in connection with IPR2013-00011: Jun. 8, 2013 Videotaped Deposition Transcript of George M. Weinstock, Ph.D.
Exhibit 1036, filed Sep. 27, 2013 in connection with IPR2013-00011: "Next Generation Genomics: World Map of High-throughput Sequencers," Sep. 1, 2013.
Exhibit 1037, filed Sep. 27, 2013 in connection with IPR2013-00011: GB Application No. 2001 0029012, filed Dec. 4, 2001 by Balasubramanian et al.
Exhibit 1039, filed Sep. 27, 2013 in connection with IPR2013-00011: Videotaped Deposition Transcript of Dr. Xiaohai Liu, Mar. 20, 2013.
Exhibit 1040, filed Sep. 27, 2013 in connection with IPR2013-00011: Excerpt from videotaped Deposition Transcript of George M. Weinstock, Ph.D., Jun. 8, 2013.
Exhibit 1041, filed Sep. 27, 2013 in connection with IPR2013-00011: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.

Exhibit 1042, filed Sep. 27, 2013 in connection with IPR2013-00011: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2013-00011: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2013-00011: Seela et al., "Duplex Stability of Oligonucleotides Containing 7-Substituted 7-Deaza- and 8-Aza-7-Deazapurine Nucleosides," Nucleosides & Nucleotides, 16(7-9), pp. 963-966, 1997.
Exhibit 1045, filed Sep. 27, 2013 in connection with IPR2013-00011: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2013-00011: U.S. Patent No. 5,151,507, issued Sep. 29, 1992 to Hobbs, Jr. et al.
Exhibit 1047, filed Sep. 27, 2013 in connection with IPR2013-00011: U.S. Patent No. 7,078,499, issued Jul. 18, 2006 to Odedra et al.
Exhibit 1048, filed Sep. 27, 2013 in connection with IPR2013-00011: GB Application No. 2000 0013276, filed Jun. 1, 2000 by Odedra et al.
Exhibit 1049, filed Sep. 27, 2013 in connection with IPR2013-00011: Jan. 28, 2013 Declaration of Dr. Bruce P. Branchaud in Support of Petition for Inter Partes Review of U.S. Patent No. 7,057,026.
Exhibit 1050, filed Sep. 27, 2013 in connection with IPR2013-00011: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2013-00011: http://www.answers.com/topic/incubate, Accessed Sep. 27, 2013.
Exhibit 1052, filed Sep. 27, 2013 in connection with IPR2013-00011: http://en.wikipedia.org/wiki/Fluorenylmethyloxycarbonyl_chloride, Accessed Sep. 27, 2013.
Exhibit 1053, filed Sep. 27, 2013 in connection with IPR2013-00011: Sep. 27, 2013 Declaration of Kevin Burgess.
Exhibit 1054, filed Sep. 27, 2013 in connection with IPR2013-00011: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Jan. 7, 2013 in connection with IPR2013-00011: Composition of a Nucleotide.
Exhibit 2006, filed Apr. 26, 2013 in connection with IPR2013-00011: Dower patent with highlights.
Exhibit 2010, filed Jun. 24, 2013 in connection with IPR2013-00011: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2013-00011: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2013-00011: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2013-00011: Oct. 2, 2012 Declaration of George Weinstock Under 37 CFR 1.132 (Exhibit 1021 in IPR2013-00011).
Exhibit 2014, filed Jun. 24, 2013 in connection with IPR2013-00011: Petition for Inter Partes Review of U.S. Pat. No. 8,088,575 (Paper 4 in IPR2013-00011).
Exhibit 2015, filed Jun. 24, 2013 in connection with IPR2013-00011: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2013-00011: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2013-00011: Sep. 15, 2012 Declaration of George Weinstock Under 37 CFR 1.132 (Exhibit 1021 in IPR2012-00007).

(56) References Cited

OTHER PUBLICATIONS

Exhibit 2018, filed Jun. 24, 2013 in connection with IPR2013-00011: Sep. 15, 2012 Declaration of George Weinstock Under 37 CFR 1.132 (Exhibit 1021 in IPR2012-00006).
Exhibit 2019, filed Jun. 24, 2013 in connection with IPR2013-00011: Definition of "DNA microarray." http:/en/wikipedia.org/wiki/DNA microarray.
Exhibit 2020, filed Jun. 24, 2013 in connection with IPR2013-00011: Brettin et al. (2005) Expression capable library for studies of Neisseria gonorrhoeae, version 1.0 BMC Microbiology. 5:50.
Exhibit 2021, filed Jun. 24, 2013 in connection with IPR2013-00011: George M. Weinstock, Handbook of Molecular Microbial Ecology, vol. 1-Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2013-00011: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2013-00011: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2013-00011: Maxam and Gilbert (1977) A new method for sequencing DNA, Proc. Natl. Acad. Sci. USA. 74:560-564.
Exhibit 2025, filed Jun. 24, 2013 in connection with IPR2013-00011: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2013-00011: Pennisi (2000) DOE Team Sequences Three Chromosomes, Science. 288:417-419.
Exhibit 2027, filed Jun. 24, 2013 in connection with IPR2013-00011: Welch and Burgess (1999) Synthesis of Fluorescent, Photolabile 3'-O-Protected nucleoside Triphosphates for the Base Addition Sequencing Scheme, nucleosides & Nucleotides.
Exhibit 2028, filed Jun. 24, 2013 in connection with IPR2013-00011: Hyman (1998) A New Method of Sequencing DNA, Analytical Biochemistry 174:423-436.
Exhibit 2029, filed Jun. 24, 2013 in connection with IPR2013-00011: U.S. Pat. No. 5,302,509 (filed Feb. 27, 1991, issued Apr. 12, 1994).
Exhibit 2030, filed Jun. 24, 2013 in connection with IPR2013-00011: Canard and Sarfati (1994) DNA polymerase fluorescent substrates with reversible 3'-tags, Gene. 1481-6.
Exhibit 2031, filed Jun. 24, 2013 in connection with IPR2013-00011: U.S. Pat. No. 8,399,188 (filed Sep. 4, 2007, issued Mar. 19, 2013).
Exhibit 2032, filed Jun. 24, 2013 in connection with IPR2013-00011: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2013-00011: Jun. 25, 2013 Substitute Declaration of Dr. George L. Trainor [redacted].
Exhibit 2034, filed Jun. 25, 2013 in connection with IPR2013-00011: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2013-00011: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2013-00011: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2013-00011: Oct. 1, 2006 Request for opinion on manuscript by J. Ju et. al., Proceedings of National Academy of Sciences, U.S.A.
Exhibit 2038, filed Jun. 25, 2013 in connection with IPR2013-00011: Correspondence between George Rupp, Chancellor, Columbia University and Richard T. Schlossberg, President, The David and Lucile Packard Foundation (2001).

Exhibit 2039, filed Jun. 25, 2013 in connection with IPR2013-00011: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 26, 2013 in connection with IPR2013-00011: "Chemistry for Next-Generation Sequencing." http://www.illumina.com/technology/sequencing technology.ilmn.
Exhibit 2041, filed Jun. 26, 2013 in connection with IPR2013-00011: Chiang et al. (2010) Mammalian microRNAs: experimental evaluation of novel and previously annotated genes, Genes & Dev. 24:992, 993.
Exhibit 2042, filed Jun. 26, 2013 in connection with IPR2013-00011: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 26, 2013 in connection with IPR2013-00011: Curriculum vitae of Mr. Raymond S. Sims.
Exhibit 2044, filed Jun. 26, 2013 in connection with IPR2013-00011: Prior Testimony of Mr. Raymond S. Sims.
Exhibit 2045, filed Jun. 26, 2013 in connection with IPR2013-00011: Documents reviewed by Mr. Raymond S. Sims in this Proceeding.
Exhibit 2052, filed Jun. 26, 2013 in connection with IPR2013-00011: Gary Schroth Proof of Chiang Paper.
Exhibit 2074, filed Jun. 26, 2013 in connection with IPR2013-00011: Information about Dr. Ju's intellectual property sent to Illumina.
Exhibit 2090, filed Jun. 26, 2013 in connection with IPR2013-00011: IPR Default Protective Order.
Exhibit 2091, filed Jun. 26, 2013 in connection with IPR2013-00011: Declaration of Raymond S. Sims.
Exhibit 2092, filed Oct. 1, 2013 in connection with IPR2013-00011: Rough transcript of the Sep. 4, 2013 deposition of Dr. George L. Trainor.
Exhibit 2093, filed Oct. 1, 2013 in connection with IPR2013-00011: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2013-00011: Final transcript of the Sep. 4-6, 2013 deposition of Dr. George L. Trainor.
Exhibit 2095, filed Oct. 1, 2013 in connection with IPR2013-00011: Final transcript of the Sep. 3, 2013 deposition of Raymond S. Sims.
Exhibit 1056, filed Nov. 19, 2013 in connection with IPR2012-00007: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in connection with IPR2012-00007.
Exhibit 2099, filed Nov. 12, 2013 in connection with IPR2013-00011: Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2013-00011: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2013-00011: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2013-00011: Advanced Sequencing Technology Awards 2004. http://www.genome.gov/12513162 (accessed Oct. 14, 2013).
Exhibit 2103, filed Nov. 12, 2013 in connection with IPR2013-00011: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Jan. 29, 2013 Petition for Inter Partes Review of U.S. Patent No. 7,057,026.

(56) References Cited

OTHER PUBLICATIONS

Feb. 7, 2013 Revised Petition for Inter Partes Review of U.S. Patent No. 7,057,026.
May 1, 2013 Preliminary Response under 37 C.F.R. 42.107 in connection with IPR2013-00128.
Jul. 29, 2013 Decision on Petition for Inter Partes Review in connection with IPR2013-00128.
Oct. 24, 2013 Patent Owner Motion to Amend the Patent in connection with IPR2013-00128.
Exhibit 1001, filed Jan. 29, 2013 in connection with IPR2013-00128: U.S. Patent No. 7,057,026 to Colin Barnes et.
Exhibit 1002, filed Jan. 29, 2013 in connection with IPR2013-00128: PCT Publication WO 00/53805 to Stemple et al.
Exhibits 1003-1005, filed Jan. 29, 2013 in connection with IPR2013-00128: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1006, filed Jan. 29, 2013 in connection with IPR2013-00128: Beckman Coulter Ceqtm 2000 DNA Analysis System User's Guide, Jun. 2000.
Exhibit 1007, filed Jan. 29, 2013 in connection with IPR2013-00128: U.S. Patent No. 5,798,210 to Canard et al.
Exhibit 1008, filed Jan. 29, 2013 in connection with IPR2013-00128: U.S. Patent No. 6,664,079 to Ju et al.
Exhibit 1009, filed Jan. 29, 2013 in connection with IPR2013-00128: PCT Publication WO 02/29003, published Apr. 11, 2002 to Ju et al.
Exhibit 1010, filed Jan. 29, 2013 in connection with IPR2013-00128: Kamal, Tetrahedron Letters 40(2):371-372, 1999.
Exhibit 1011, filed Jan. 29, 2013 in connection with IPR2013-00128: Jung, J.C.S. Chem. Comm. (7):315-316, 1978.
Exhibit 1012, filed Jan. 29, 2013 in connection with IPR2013-00128: PCT Publication WO 91/06678, published May 16, 1991 to Tsien et al.
Exhibit 1013, filed Jan. 29, 2013 in connection with IPR2013-00128: Prober et al., Science 238, 336-341 (1987).
Exhibit 1014, filed Jan. 29, 2013 in connection with IPR2013-00128: U.S. Patent No. 5,547,839, issued Aug. 20, 1996 to Dowler et al.
Exhibit 1015, filed Jan. 29, 2013 in connection with IPR2013-00128: Jan. 28, 2013 Declaration of Dr. Bruce Branchaud.
Exhibit 1016, filed Jan. 29, 2013 in connection with IPR2013-00128: Excerpts from the '026 Patent File History.
Exhibit 1017, filed Jan. 29, 2013 in connection with IPR2013-00128: Sep. 16, 2012 Petition for Inter Partes Review of U.S. Patent No. 7,713,698.
Exhibit 1018, filed Jan. 29, 2013 in connection with IPR2013-00128: Sep. 16, 2012 Petition for Inter Partes Review of U.S. Patent No. 7,790,869.
Exhibit 1019, filed Jan. 29, 2013 in connection with IPR2013-00128: Oct. 3, 2012 Petition for Inter Partes Review of U.S. Patent No. 8,088,575.
Exhibit 1020, filed Jan. 29, 2013 in connection with IPR2013-00128: Transcript of Initial Conference Call Held on Aug. 29, 2013.
Exhibit 2001, filed May 1, 2013 in connection with IPR2013-00128: *The Trustees of Columbia University in the City of New York v. Illumina, Inc.*, 1:12-cv-00376-GMS—Columbia's Amended Complaint.
Exhibit 2002, filed May 1, 2013 in connection with IPR2013-0128: *The Trustees of Columbia University in the City of New York v. Illumina, Inc.*, 1:12-cv-00376-GMS—Columbia's Amended Answer.
Exhibit 2003, filed May 1, 2013 in connection with IPR2013-00128: *The Trustees of Columbia University in the City of New York v. Illumina, Inc.*, 1:12-cv-00376-GMS- IBS's Responses to Illumina's Requests for Admission.
Exhibit 2004, filed May 1, 2013 in connection with IPR2013-00128: *The Trustees of Columbia University in the City of New York v. Illumina, Inc.*, 1:12-cv-00376-GMS—Columbia's Response to Illumina's Requests for Admission.
Exhibit 2006, filed Oct. 24, 2013 in connection with IPR2013-00128: Green & Wuts, Protective Groups in Organic Synthesis, excerpts from "Protection From the Hydroxyl Group," (1999).
Exhibit 2007, filed Oct. 24, 2013 in connection with IPR2013-00128: Katagiri et al., "Selective Protection of the Primary Hydroxyl Groups of Oxetanocin A," Chem. Pharm. Bull. 43:884-886 (1995).
Exhibit 2008, filed Oct. 24, 2013 in connection with IPR2013-00128: U.S. Appl. No. 10/227,131, filed Aug. 23, 2002.
Exhibits 2009, 2010, and 2011, filed Oct. 24, 2013 in connection with IPR2013-00128: Declaration of Floyd Romesberg, Ph.D., Romesburg CV, and Romesburg list of documents reviewed.
Exhibit 2012, filed Oct. 24, 2013 in connection with IPR2013-00128: Oct. 3, 2013 Deposition Transcript of Bruce Branchaud, Ph.D.
Exhibit 2013, filed Oct. 24, 2013 in connection with IPR2013-00128: U.S. Patent No. 7,078,499—Odedra, filed Mar. 24, 2003.
Exhibit 2014, filed Oct. 24, 2013 in connection with IPR2013-00128: PCT International Publication No. WO 01/92284—Odedra, published Dec. 6, 2001.
Exhibit 2015, filed Oct. 24, 2013 in connection with IPR2013-00128: PCT International Publication No. WO 96/27025—Rabini, published Sep. 6, 1996.
Exhibit 2016, filed Oct. 24, 2013 in connection with IPR2013-00128: Ruby, Methods in Enzymology (1990).
Exhibit 2017, filed Oct. 24, 2013 in connection with IPR2013-00128: U.S. Patent No. 4,772,691—Herman, filed Jun. 5, 1985.
Exhibit 2018, filed Oct. 24, 2013 in connection with IPR2013-00128: PCT International Publication No. WO 99/49082—Short, published Sep. 30, 1999.
Exhibit 2019, filed Oct. 24, 2013 in connection with IPR2013-00128: Sanger, "DNA Sequencing with Chain-Inhibiting Terminators" PNAS 74(12):6463-5467 (1977).
Exhibit 2020, filed Oct. 24, 2013 in connection with IPR2013-00128: U.S. Patent No. 5,302,509—Cheeseman, filed Feb. 27, 1991.
Exhibit 2021, filed Oct. 24, 2013 in connection with IPR2013-00128: Metzker, "Termination of DNA synthesis by novel 3'-modified deoxyribonucleoside 5'-triphosphates", Nucleic Acids Research 22(20): 4259-4267 (1994).
Exhibit 2022, filed Oct. 24, 2013 in connection with IPR2013-00128: Welch & Burgess, Nucleosides and Nucleotides, 18:197-201 (1999).
Exhibit 2023, filed Oct. 24, 2013 in connection with IPR2013-00128: Jun. 4, 2013 Declaration of Bruce Branchaud, Ph.D. in IPR2013-00324.
Exhibit 2024, filed Oct. 24, 2013 in connection with IPR2013-00128: PCT International Publication No. WO 89/10977—Southern, published Nov. 16, 1989.
Exhibit 2025, filed Oct. 24, 2013 in connection with IPR2013-00128: U.S. Patent No. 7,057,026 file history.
Exhibit 2026, filed Oct. 24, 2013 in connection with IPR2013-00128: Maxam and Gilbert, "A New Method for Sequencing DNA" 74:560-564, PNAS (1977).
Exhibit 2028, filed Oct. 24, 2013 in connection with IPR2013-00128: Eric Vermaas Declaration, Oct. 24, 2013.
May 4, 2013 Petition for Inter Partes Review of U.S. Patent No. 8,158,346, issued Apr. 17, 2012.
Aug. 5, 2013 Patent Owner Preliminary Response to Petition for Inter Partes Review of U.S. Patent No. 8,158,246, issued Apr. 17, 2012.
Exhibit 1001, filed May 4, 2013 in connection with IPR2013-00266: U.S. Patent No. 8,158,346, issued Apr. 17, 2012 to Shankar Balasubramanian et al.
Exhibit 1002, filed May 4, 2013 in connection with IPR2013-00266: U.S. Patent No. 6,664,079, issued Dec. 16, 2003 to Jingyue Ju et al.
Exhibit 1003, filed May 4, 2013 in connection with IPR2013-00266: WO 02/29003, published Apr. 11, 2002 to Jingyue Ju et.
Exhibit 1004, filed May 4, 2013 in connection with IPR2013-00266: Kamal et al., A Mild and Rapid Regeneration of Alcohols from their Allylic Ethers by Chlorotrimethylsilane/Sodium Iodide, 40 Tetrahedron Letters 371 (1999).
Exhibit 1005, filed May 4, 2013 in connection with IPR2013-00266: Jung et al., Conversion of Alkyl Carbamates into Amines vie Treatment with Trimethylsilyl Iodide, 7 J.C.S. Chem. Comm. 315 (1978).
Exhibit 1006, filed May 4, 2013 in connection with IPR2013-00266: WO 91/06678, published May 16, 1991 to Roger Tsien et al.

(56) References Cited

OTHER PUBLICATIONS

Exhibit 1007, filed May 4, 2013 in connection with IPR2013-00266: WO 00/53805, published Sep. 14, 2000 to Derek Stemple et al.
Exhibit 1008, filed May 4, 2013 in connection with IPR2013-00266: U.S. Patent No. 7,078,499, issued Jul. 18, 2006 to Raj Odedra et al.
Exhibit 1009, filed May 4, 2013 in connection with IPR2013-00266: WO 01/92284, published Dec. 6, 2001 to Raj Odedra et al.
Exhibit 1010, filed May 4, 2013 in connection with IPR2013-00266: U.S. Patent No. 5,547,839, issued Aug. 20, 1996 to William Dower et al.
Exhibit 1011, filed May 4, 2013 in connection with IPR2013-00266: May 3, 2013 Declaration of Dr. Bruce Branchaud.
Exhibit 1012, filed May 4, 2013 in connection with IPR2013-00266: Excerpts from the '346 Patent File History.
Exhibit 1013, filed May 4, 2013 in connection with IPR2013-00266: Excerpts from the file history of European Patent Application No: 02781434.2.
Exhibit 1014, filed May 4, 2013 in connection with IPR2013-00266: Sep. 16, 2013 Petition for Inter Partes Review of U.S. Patent No. 7,713,698.
Exhibit 1015, filed May 4, 2013 in connection with IPR2013-00266: Sep. 16, 2013 Petition for Inter Partes Review of U.S. Patent No. 7,790,869.
Exhibit 1016, filed May 4, 2013 in connection with IPR2013-00266: Oct. 3, 2013 Petition for Inter Partes Review of U.S. Patent No. 8,088,575.
Exhibit 2001, filed Aug. 5, 2013 in connection with IPR2013-00266: Columbia's Apr. 11, 2012 Amended Complaint in connection with case No. C.A. No.: 12-376-GMS.
Exhibit 2002, filed Aug. 5, 2013 in connection with IPR2013-00266: Columbia's Jan. 7, 2013 Amended Answer in connection with case No. C.A. No.: 12-376-GMS.
Jun. 4, 2013 Petition for Inter Partes Review of U.S. Patent No. 7,057,026.
Exhibit 1001, filed Jun. 4, 2013 in connection with IPR2013-00324: U.S. Patent No. 7,057,026, issued Jun. 6, 2006 to Colin Barnes et al.
Exhibit 1002, filed Jun. 4, 2013 in connection with IPR2013-00324: U.S. Patent No. 7,078,499, issued Jul. 18, 2006 to Raj Odedra et al.
Exhibit 1003, filed Jun. 4, 2013 in connection with IPR2013-00324: WO 01/92284, published Dec. 6, 2001 to Raj Odedra et al.
Exhibit 1004, filed Jun. 4, 2013 in connection with IPR2013-00324: J. Meinwald, An Approach to the Synthesis of Pederin, 49 Pure and Appl. Chem. 1275 (1977).
Exhibit 1005, filed Jun. 4, 2013 in connection with IPR2013-00324: Takeshi Matsumoto et al., A Revised Structure of Pederin, 60 Tetrahedron Letters 6297 (1968).
Exhibit 1006, filed Jun. 4, 2013 in connection with IPR2013-00324: U.S. Patent No. 5,547,839, issued Aug. 20, 1996 to William Dower et al.
Exhibit 1007, filed Jun. 4, 2013 in connection with IPR2013-00324: U.S. Patent No. 5,798,210, issued Aug. 25, 1998 to Bruno Canard & Simon Sarfati.
Exhibit 1008, filed Jun. 4, 2013 in connection with IPR2013-00324: Beckman Coulter CEQTM 2000 DNA Analysis System User's Guide, Jun. 2000.
Exhibit 1009, filed Jun. 4, 2013 in connection with IPR2013-00324: Jun. 4, 2013 Declaration of Dr. Bruce Branchaud.
Exhibit 1010, filed Jun. 4, 2013 in connection with IPR2013-00324: Excerpts from the '026 Patent File History.
Exhibit 1011, filed Jun. 4, 2013 in connection with IPR2013-00324: Excerpts from the file history of European Patent Application No: 02781434.2.
Aug. 19, 2013 Petition 1 of 2 for Inter Partes Review of U.S. Patent No. 7,566,537, issued Jul. 28, 2009.
Aug. 30, 2013 Revised Petition 1 of 2 for Inter Partes Review of U.S. Patent No. 7,566,537, issued Jul. 28, 2009.
Exhibit 1001, filed Aug. 19, 2013 in connection with IPR2013-00517: U.S. Patent No. 7,566,537, issued Jul. 28, 2009 to Shankar Balasubramanian et al.
Exhibit 1002, filed Aug. 19, 2013 in connection with IPR2013-00517: U.S. Patent No. 6,664,079, issued Dec. 16, 2003 to Jingyue Ju et al.
Exhibit 1003, filed Aug. 19, 2013 in connection with IPR2013-00517: U.S. Appl. No. 09/684,670, filed Oct. 6, 2000 by Jingyue Ju et al.
Exhibit 1004, filed Aug. 19, 2013 in connection with IPR2013-00517: Zavgorodny et al., 1-Alkylthioalkylation of Nucleoside Hydroxyl Functions and Its Synthetic Applications: A New Versatile Method in Nucleoside Chemistry, 32 Tetrahedron Letters 7593 (1991).
Exhibit 1005, filed Aug. 19, 2013 in connection with IPR2013-00517: Protective Groups in Organic Synthesis (Theodora W. Greene & Peter G. M. Wuts eds., John Wiley & Sons, Inc. 3rd ed. 1999) (1991).
Exhibits 1006-1007, filed Aug. 19, 2013 in connection with IPR2013-00517: English translation of Loubinoux et al., Protection of Phenols by the Azidomethylene Group Application to the Synthesis of Unstable Phenols, 44 Tetrahedron 6055 (1988), and Translation Affidavit.
Exhibit 1008, filed Aug. 19, 2013 in connection with IPR2013-00517: WO 91/06678, published May 16, 1991 to Roger Tsien et al.
Exhibit 1009, filed Aug. 19, 2013 in connection with IPR2013-00517: Prober et al., A System for Rapid DNA Sequencing with Fluorescent Chain-Terminating Dideoxynucleotides, 238 Science 336 (1987).
Exhibit 1010, filed Aug. 19, 2013 in connection with IPR2013-00517: P 0251786 B1, issued Nov. 30, 1994 to George Leonard Trainor.
Exhibit 1011, filed Aug. 19, 2013 in connection with IPR2013-00517: Aug. 16, 2013 Declaration of Dr. Bruce Branchaud.
Exhibit 1012, filed Aug. 19, 2013 in connection with IPR2013-00517: Excerpts from the Mar. 20, 2013 Deposition Transcripy of Dr. Xiaohai Liu.
Exhibit 1013, filed Aug. 19, 2013 in connection with IPR2013-00517: Sep. 16, 2012 Petition for Inter Partes Review of U.S. Patent No. 7,713,698.
Exhibit 1014, filed Aug. 19, 2013 in connection with IPR2013-00517: Sep. 16, 2012 Petition for Inter Partes Review of U.S. Patent No. 7,790,869.
Exhibit 1015, filed Aug. 19, 2013 in connection with IPR2013-00517: Oct. 3, 2012 Petition for Inter Partes Review of U.S. Patent No. 8,088,575.
Aug. 19, 2013 Petition 2 of 2 for Inter Partes Review of U.S. Patent No. 7,566,537, issued Aug. 19, 2013.
Exhibit 1001, filed Aug. 19, 2013 in connection with IPR2013-00518: U.S. Patent No. 7,566,537, issued Jul. 28, 2009 to Shankar Balasubramanian et al.
Exhibit 1002, filed Aug. 19, 2013 in connection with IPR2013-00518: U.S. Patent No. 6,664,079, issued Dec. 16, 2003 to Jingyue Ju et al.
Exhibit 1003, filed Aug. 19, 2013 in connection with IPR2013-00518: U.S. Appl. No. 09/684,670, filed Oct. 6, 2000 by Jingyue Ju et al.
Exhibit 1004, filed Aug. 19, 2013 in connection with IPR2013-00518: Kamal et al., A Mild and Rapid Regeneration of Alcohols from their Allylic Ethers by Chlorotrimethylsilane/Sodium Iodide, 40 Tetrahedron Letters 371 (1999).
Exhibit 1005, filed Aug. 19, 2013 in connection with IPR2013-00518: Jung et al., Conversion of Alkyl Carbamates via Treatment with Trimethylsilyl Iodide, 7 J.C.S. Chem. Comm. 315 (1978).
Exhibit 1006, filed Aug. 19, 2013 in connection with IPR2013-00518: WO 91/06678, issued May 16, 1991 to Roger Tsien et al.
Exhibit 1007, filed Aug. 19, 2013 in connection with IPR2013-00518: Prober et al., A System for Rapid DNA Sequencing with Fluorescent Chain-Terminating Dideoxynucleotides, 238 Science 336 (1987).
Exhibit 1008, filed Aug. 19, 2013 in connection with IPR2013-00518: WO 00/53805, issued Sep. 14, 2000 to Derek Stemple et al.
Exhibits 1009-1010, filed Aug. 19, 2013 in connection with IPR2013-00518: English translation of Takeshi Anazawa et al., WO 98/33939 (Aug. 6, 1998) and Translation Affidavit (Submitted by Illumina, Inc. as Exhibits 1011-1012 in IPR2012-00007).

(56) References Cited

OTHER PUBLICATIONS

Exhibit 1011, filed Aug. 19, 2013 in connection with IPR2013-00518: U.S. Patent No. 7,078,499, issued Jul. 18, 2006 to Raj Odedra et al.
Exhibit 1012, filed Aug. 19, 2013 in connection with IPR2013-00518: WO 01/92284, published Dec. 6, 2001 to Raj Odedra et al.
Exhibit 1013, filed Aug. 19, 2013 in connection with IPR2013-00518: U.S. Patent No. 5,547,839, issued Aug. 20, 1996 to William Dower et al.
Exhibit 1014, filed Aug. 19, 2013 in connection with IPR2013-00518: EP 0251786 B1, issued Nov. 30, 1994 to George Leonard Trainor.
Exhibit 1015, filed Aug. 19, 2013 in connection with IPR2013-00518: Aug. 16, 2013 Declaration of Dr. Bruce Branchaud.
Exhibit 1016, filed Aug. 19, 2013 in connection with IPR2013-00518: Excerpts from the '537 Patent File History.
Exhibit 1017, filed Aug. 19, 2013 in connection with IPR2013-00518: Excerpts from the file history of European Patent Application No: 02781434.2.
Exhibit 1018, filed Aug. 19, 2013 in connection with IPR2013-00518: Sep. 16, 2012 Petition for Inter Partes Review of U.S. Patent No. 7,713,698.
Exhibit 1019, filed Aug. 19, 2013 in connection with IPR2013-00518: Sep. 16, 2012 Petition for Inter Partes Review of U.S. Patent No. 7,790,869.
Exhibit 1020, filed Aug. 19, 2013 in connection with IPR2013-00518: Sep. 16, 2012 Petition for Inter Partes Review of U.S. Patent No. 8,088,575.
Oct. 28, 2013 Decision Instituting Inter Partes Review in connection with IPR2013-00266.
Nov. 26, 2013 Petitioner Response to Motion for Observations in connection with IPR2012-00006.
Nov. 26, 2013 Patent Owner Opposition to Petitioner's Motion to Exclude in connection with IPR2012-00006.
Nov. 26, 2013 Petitioner Opposition to Motion to Exclude in connection with IPR2012-00006.
Dec. 3, 2013 Petitioner Reply to Patent Owner's Opposition to Motion to Exclude in connection with IPR2012-00006.
Dec. 3, 2013 Patent Owner Reply on Motion to Exclude in connection with IPR2012-00006.
Nov. 26, 2013 Petitioner's Response to Motion for Observations in connection with IPR2012-00007.
Nov. 26, 2013 Patent Owner's Opposition to Petitioner's Motion to Exclude in connection with IPR2012-00007.
Nov. 26, 2013 Petitioner's Opposition to Motion to Exclude in connection with IPR2012-00007.
Dec. 3, 2013 Petitioner Reply to Patent Owner's Opposition to Motion to Exclude in connection with IPR2012-00007.
Dec. 3, 2013 Patent Owner Reply on Motion to Exclude in connection with IPR2012-00007.
Nov. 26, 2013 Petitioner's Response to Motion for Observations in connection with IPR2013-00011.
Nov. 26, 2013 Patent Owner's Opposition to Petitioner's Motion to Exclude in connection with IPR2013-00011.
Nov. 26, 2013 Petitioner's Opposition to Motion to Exclude in connection with IPR2013-00011.
Dec. 3, 2013 Petitioner Reply to Patent Owner's Opposition to Motion to Exclude in connection with IPR2013-00011.
Dec. 3, 2013 Patent Owner Reply on Motion to Exclude in connection with IPR2013-00011.
Record of Dec. 17, 2013 Oral Hearing, entered Feb. 10, 2014 in connection with IPR2012-00006, IPR2012-00007, and IPR2013-00011.
Mar. 6, 2014 Final Written Decision in connection with IPR2012-00006.
Mar. 6, 2014 Final Written Decision in connection with IPR2012-00007.
Mar. 6, 2014 Final Written Decision in connection with IPR2013-00011.

Jan. 24, 2014 Intelligent Bio-Systems Opposition to Illumina's Motion to Amend in connection with IPR2013-00128.
Exhibit 1030, filed Jan. 24, 2014 in connection with IPR2013-00128: Dawson et al., "Affinity Isolation of Transcriptionally Active Murine Erythroleukemia Cell DNA Using a Cleavable Biotinylated Nucleotide Analog" J. of Biol. Chem., 264, 12830-37 (1989).
Exhibit 1032, filed Jan. 24, 2014 in connection with IPR2013-00128: Mitra et al., "Fluorescent in situ sequencing on polymerase colonies" Analytical Biochem. 320, 55-65 (2003).
Exhibit 1033, filed Jan. 24, 2014 in connection with IPR2013-00128: Deposition of Floyd Romesberg, Ph.D., from Jan. 14, 2014.
Exhibit 1034, filed Jan. 24, 2014 in connection with IPR2013-00128: 1999/2000 Pierce Chemical Company catalog (1999).
Exhibit 1035, filed Jan. 24, 2014 in connection with IPR2013-00128: Second Declaration of Dr. Bruce Branchaud, dated Jan. 23, 2014.
Exhibit 1039, filed Jan. 24, 2014 in connection with IPR2013-00128: Excerpts from the file history of European Patent Application No: 02781434.2.
Exhibit 1041, filed Jan. 24, 2014 in connection with IPR2013-00128: Lukesh et al., "A Potent, Versatile Disulfide-Reducing Agent from Aspartic Acid" J. Am. Chem. Soc., 134, 4057-59 (2012).
Exhibit 1042, filed Jan. 24, 2014 in connection with IPR2013-00128: Klausner, "Dupont's DNA Sequencer Uses New Chemistry" Nat. Biotech., 5, 1111-12 (1987).
Exhibit 1043, filed Jan. 24, 2014 in connection with IPR2013-00128: Murakami et al., "Structure of a Plasmodium yoelii gene-encoded protein homologous to the Ca2+-ATPase of rabbit skeletal muscle sarcoplasmic reticulum" J. Cell Sci., 97, 487-95 (1990).
Exhibit 1044, filed Jan. 24, 2014 in connection with IPR2013-00128: Letsinger et al., "2,4-Dinitrobenzenesulfenyl as a Blocking Group for Hydroxyl Functions in Nucleosides" J. Org. Chem., 29, 2615-2618 (1964).
Exhibit 1045, filed Jan. 24, 2014 in connection with IPR2013-00128: Handlon & Oppenheimer, "Thiol Reduction of 3'-Azidothymidine to 3'-Aminothymidine: Kinetics and Biomedical Implications" Pharm. Res., 5, 297-99 (1988).
Exhibit 1047, filed Jan. 24, 2014 in connection with IPR2013-00128: Burns et al., "Selective Reduction of Disulfides by Tris(2-carboxyethyl)phosphine" J. Org. Chem., 56, 2648-50 (1991).
Feb. 19, 2014 Substitute Motion to Amend Under 37 C.F.R. §42.121 in connection with IPR2013-00128.
Exhibit 2009, filed Feb. 19, 2014 in connection with IPR2013-00128: Substitute Declaration of Floyd Romesberg, Ph.D., in Support of Patent Owner's Motion to Amend.
Exhibit 2028, filed Feb. 19, 2014 in connection with IPR2013-00128: Substitute Declaration of Eric Vermaas Accompanying Patent Owner's Motion to Amend.
Feb. 24, 2014 Patent Owner Illumina's Reply to Petitioner's Opposition to Illumina's Motion to Amend.
Exhibit 2029, filed Feb. 24, 2014 in connection with IPR2013-00128: Supplementary information for Ex. 1032 (Mitra et al., Analytical Biochem. 320, 55-65, 2003).
Exhibit 2031, filed Feb. 24, 2014 in connection with IPR2013-00128: Ju et al., "Four-color DNA 15 Sequencing By Synthesis Using Cleavable 16 Fluorescent Nucleotide Reversible Terminators," PNAS USA, 103:19635-19640 (2006).
Exhibit 2032, filed Feb. 24, 2014 in connection with IPR2013-00128: ScanArray Express Line of Microarray Scanners—Brochure.
Exhibit 2034, filed Feb. 24, 2014 in connection with IPR2013-00128: Feb. 11, 2014 Second Deposition Transcript of Bruce Branchaud, Ph.D.
Exhibit 2037, filed Feb. 24, 2014 in connection with IPR2013-00128: Mullis et al., "Specific Synthesis of DNA in Vitro via a Polymerase-Catalyzed Chain Reaction," pp. 335-350, in Methods in Enzymology, vol. 155, Recombinant DNA, Part F, ed. Wu, Academic Press, Inc., San Diego (1987).
Exhibit 2038, filed Feb. 24, 2014 in connection with IPR2013-00128: Brown et al., "Modern machine-aided methods of oligodeoxyribonucleotide synthesis," pp. 1-11; and Ruth, "Oligodeoxynucleotides with reporter groups attached to the base," p. 255, in Oligonucleotides and Analogues, A Practical Approach, ed. Eckstein, Oxford Univ. Press, New York (1991).

(56) References Cited

OTHER PUBLICATIONS

Exhibit 2039, filed Feb. 24, 2014 in connection with IPR2013-00128: Dawson and Herman et al., "Affinity isolation of active murine erythroleukemia cell chromatin: Uniform distribution of ubiquitinated histone H2A between active and inactive fractions", Journal of Cellular Biochemistry 46:166-173 (1991).
Exhibit 2040, filed Feb. 24, 2014 in connection with IPR2013-00128: Rigas et al., "Rapid plasmid library screening using RecA-coated biotinylated probes," PNAS USA 83:9591-9595 (1986).
Exhibit 2042, filed Feb. 24, 2014 in connection with IPR2013-00128: Westheimer et al., "Why nature chose phosphates" Science 235:1173-1178 (1987).
Mar. 18, 2014 Petitioner's Motion to Exclude in connection with IPR2013-00128.
Exhibit 1048, filed Mar. 18, 2014 in connection with IPR2013-00128: Petitioner's Objections to Patentee's Exhibits submitted with its Reply to Petitioner's Opposition to Patentee's Motion to Amend.
Mar. 18, 2014 Patentee's Motion to Exclude Petitioner's Evidence in connection with IPR2013-00128.
Petitioner's Feb. 28, 2014 Opposition to Patentee Motion to Amend in connection with IPR2013-00266.
Exhibit 1020, filed Feb. 28, 2014 in connection with IPR2013-00266: Mitra et al, "Fluorescent in situ sequencing on polymerase colonies" Analytical Biochem. 320:55-65 (2003).
Exhibit 1021, filed Feb. 28, 2014 in connection with IPR2013-00266: Second Declaration of Dr. Bruce Branchaud in support of Intelligent Bio-Systems, Inc.'s Opposition to Illumina's Motion to Amend, from Feb. 28, 2014.
Exhibit 1022, filed Feb. 28, 2014 in connection with IPR2013-00266: Deposition of Floyd Romesberg, Ph.D., from Jan. 14, 2014.
Exhibit 1027, filed Feb. 28, 2014 in connection with IPR2013-00266: Dawson et al., "Affinity Isolation of Transcriptionally Active Murine Erythroleukemia Cell DNA Using a Cleavable Biotinylated Nucleotide Analog" J. of Biol. Chem., 264:12830-37 (1989).
Exhibit 1028, filed Feb. 28, 2014 in connection with IPR2013-00266: Canard et al., "DNA polymerase fluorescent substrates with reversible 3'-tags" Gene, 148:1-6 (1994).
Exhibit 1029, filed Feb. 28, 2014 in connection with IPR2013-00266: Deposition of Eric Vermaas from Jan. 13, 2014.
Exhibit 1031, filed Feb. 28, 2014 in connection with IPR2013-00266: Lukesh et al., "A Potent, Versatile Disulfide-Reducing Agent from Aspartic Acid" J. Am. Chem. Soc., 134:4057-59 (2012).
Exhibit 1032, filed Feb. 28, 2014 in connection with IPR2013-00266: Prober et al., "A System for Rapid DNA Dideoxynucleotides" Science, 238:336-341 (1987).
Exhibit 1033, filed Feb. 28, 2014 in connection with IPR2013-00266: Klausner, Nat. Biotech., "DuPont's New DNA Sequencer Uses New Chemistry" 5:1111-12 (1987).
Exhibit 1034, filed Feb. 28, 2014 in connection with IPR2013-00266: Murakami, et al., "Structure of a *Plasmodium yoelii* gene-encoded protein homologous to the $Ca^{2+}$-ATPase of rabbit skeletal muscle sarcoplasmic reticulum" J. Cell Sci., 97, 487-95 (1990).
Exhibit 1035, filed Feb. 28, 2014 in connection with IPR2013-00266: Excerpts from Protective Groups in Organic Synthesis (Theodora W. Greene & Peter G. M. Wuts eds., John Wiley & Sons, Inc. 3rd ed. 1999) (1991).
Exhibit 1036, filed Feb. 28, 2014 in connection with IPR2013-00266: Letsinger, et al., "2,4-Dinitrobenzenesulfenyl as a Blocking Group for Hydroxyl Functions in Nucleosides" J. Org. Chem., 29, 2615-2618 (1964).
Exhibit 1037, filed Feb. 28, 2014 in connection with IPR2013-00266: Handlon & Oppenheimer, "Thiol Reduction of 3'-Azidothymidine to 3'-Aminothymidine: Kinetics and Biomedical Implications" Pharm. Res., 5:297-99 (1988).
Exhibit 1038, filed Feb. 28, 2014 in connection with IPR2013-00266: Zavgorodny et al., "1-Alkylthioalkylation of Nucleoside Hydroxyl Functions and Its Synthetic Applications: A New Versatile Method in Nucleoside Chemistry" 32 Tetrahedron Letters 7593 (1991).

Exhibit 1039, filed Feb. 28, 2014 in connection with IPR2013-00266: Burns, et al., "Selective Reduction of Disulfides by Tris(2-carboxyethyl)phosphine" J. Org. Chem., 56, 2648-50 (1991).
Mar. 21, 2014 Patent Owner's Reply to Petitioner's Opposition to Patent Owner's Motion to Amend in connection with IPR2013-00266.
Exhibit 2030, filed Mar. 21, 2014 in connection with IPR2013-00266: Mar. 11, 2014 Bruce Branchaud Deposition Transcript.
Exhibit 2032, filed Mar. 21, 2014 in connection with IPR2013-00266: Excerpts from Feb. 11, 2014 Bruce Branchaud Deposition Transcript in related IPR2013-00128.
Exhibit 2034, filed Mar. 21, 2014 in connection with IPR2013-00266: ScanArray Express Line of Microarray Scanners—Brochure.
Exhibit 2036, filed Mar. 21, 2014 in connection with IPR2013-00266: Supplementary information for Ex. 1020 (Mitra et al., Analytical Biochem. 320, 55-65, 2003).
Exhibit 2038, filed Mar. 21, 2014 in connection with IPR2013-00266: Dawson and Herman et al., "Affinity Isolation of Active Murine Erythroleukemia Cell Chromatin: Uniform Distribution of Ubiquitinated Histone H2A Between Active and Inactive Fractions" Journal of Cellular Biochemistry 46:166-173 (1991).
Exhibit 2039, filed Mar. 21, 2014 in connection with IPR2013-00266: Rigas et al., "Rapid plasmid library screening using RecA-coated biotinylated probes" PNAS USA 83:9591-9595 (1986).
Exhibit 2043, filed Mar. 21, 2014 in connection with IPR2013-00266: English translation of Loubinoux et al., "Protection of Phenols by the Azidomethylene Group Application to the Synthesis of Unstable Phenols" Tetrahedron, 44:6055-6064 (1988).
Exhibit 2044, filed Mar. 21, 2014 in connection with IPR2013-00266: Excerpts from Oct. 3, 2013 Bruce Branchaud Deposition Transcript in related Inter Partes Review IPR2013-00128.
Exhibit 2045, filed Mar. 21, 2014 in connection with IPR2013-00266: Welch et al., "Syntheses of Nucleosides Designed for Combinatorial DNA Sequencing" Chem. Eur. J., 5:951-960 (1999).
Exhibit 2046, filed Mar. 21, 2014 in connection with IPR2013-00266: Welch et al., Corrigenda to "Syntheses of Nucleosides Designed for Combinatorial DNA Sequencing" Chem. Eur. J., 11:7145 (2005).
Exhibit 2047, filed Mar. 21, 2014 in connection with IPR2013-00266: Wu et al., "Termination of DNA synthesis by $N^6$-alkylated, not 3'-O-alkylated, photocleavable 2'-deoxyadenosine triphosphates", Nucleic Acids Research 35:6339-6349 (2007).
Exhibit 2048, filed Mar. 21, 2014 in connection with IPR2013-00266: Taylor et al., "Rise per base pair in helices of double-stranded rotavirus RNA determined by electron microscopy" Virus Research, 2:175-182 (1985).
Exhibit 2049, filed Mar. 21, 2014 in connection with IPR2013-00266: Watson et al., Molecular Biology of the Gene, Fifth Edition, Chapter 6 (2004).
Exhibit 2050, filed Mar. 21, 2014 in connection with IPR2013-00266: Shen et al., "RNA structure at high resolution" FASEB J., 9:1023-1033 (1995).
Exhibit 2051, filed Mar. 21, 2014 in connection with IPR2013-00266: Holtzman et al., "Electron microscopy of complexes of isolated acetylcholine receptor, biotinyl-toxin, and avidin" Proc. Natl. Acad. Sci. USA, 79:310-314 (1982).
Exhibit 2052, filed Mar. 21, 2014 in connection with IPR2013-00266: Pugliese et al., "Three-dimensional Structure of the Tetragonal Crystal Form of Egg-white Avidin in its Functional Complex with Biotin at 2.7 Angstrom Resolution" Journal of Molecular Biology, 231:698-710 (1993).
Exhibit 2053, filed Mar. 21, 2014 in connection with IPR2013-00266: Fersht, "Fidelity of replication of phage φX174 DNA by DNA polymerase III holoenzyme: Spontaneous mutation by misincorporation" Proc. Natl. Acad. Sci. USA, 76:4946-4950 (1979).
Exhibit 2054, filed Mar. 21, 2014 in connection with IPR2013-00266: Fersht et al., "DNA polymerase accuracy and spontaneous mutation rates: Frequencies of purine-purine, purine-pyrimidine, and pyrimidine-pyrimidine mismatches during DNA replication" Proc. Natl. Acad. Sci. USA, 78:4251-4255 (1981).
Exhibit 2055, filed Mar. 21, 2014 in connection with IPR2013-00266: Bebenek et al., "Frameshift errors initiated by nucleotide misincorporation" Proc. Natl. Acad. Sci. USA, 87:4946-4950 (1990).

(56) References Cited

OTHER PUBLICATIONS

Exhibit 2056, filed Mar. 21, 2014 in connection with IPR2013-00266: Bebenek et al., "The Effects of dNTP Pool Imbalances on Frameshift Fidelity during DNA Replication" J. Biol. Chem., 267:3589-3596 (1992).

Exhibit 2057, filed Mar. 21, 2014 in connection with IPR2013-00266: Greene and Wuts, Protective Groups in Organic Synthesis, 3rd ed., Chapter 1 (1999).

Feb. 13, 2014 Decision of Institution of Inter Partes Review IPR2013-00517.

Feb. 13, 2014 Decision of Institution of Inter Partes Review IPR2013-00518.

Demonstrative Exhibits of Intelligent Bio-Systems, Inc., for Apr. 23, 2014 hearing, filed Apr. 18, 2014 in connection with IPR2013-00128.

Demonstrative Exhibits of Illumina for Apr. 23, 2014 hearing, filed Apr. 21, 2014 in connection with IPR2013-00128.

Apr. 18, 2014 Petitioner Motion for Observations on the Cross-Examination Testimony of Dr. Romesberg, in connection with IPR2013-00266.

Apr. 18, 2014 Petitioner Motion to Exclude Evidence in connection with IPR2013-00266.

Exhibit 1042, filed Apr. 18, 2014 in connection with IPR2013-00266: Apr. 10, 2014 transcript of Deposition of Floyd Romesberg.

Apr. 18, 2014 Patentee Motion to Exclude Evidence in connection with IPR2013-00266.

* cited by examiner

Scheme A

Scheme B

Scheme C

Scheme D

CHEMICALLY CLEAVABLE 3'-O-ALLYL-DNTP-ALLYL-FLUOROPHORE FLUORESCENT NUCLEOTIDE ANALOGUES AND RELATED METHODS

This application is a §371 national stage of PCT International Application No. PCT/US2006/042739, filed Oct. 31, 2006, and claims the benefit of U.S. Provisional Application No. 60/732,040, filed Oct. 31, 2005, the contents of all of which are hereby incorporated by reference into this application.

This invention was made with Government support under Center of Excellence in Genomic Science Grant No. 1P50 HG002806-01 awarded by the National Institutes of Health, U.S. Department of Health and Human Services. Accordingly, the U.S. Government has certain rights in this invention.

Throughout this application, various publications are referenced in parentheses by number. Full citations for these references may be found at the end of each experimental section. The disclosures of these publications in their entireties are hereby incorporated by reference into this application to more fully describe the state of the art to which this invention pertains.

BACKGROUND OF THE INVENTION

With the completion of human genome project, there is now a focus on developing new DNA sequencing technology that will reduce the cost of sequencing dramatically without sacrificing accuracy, which will ultimately enable personalized medicine in healthcare (1). Current state-of-the-art DNA sequencing technology faces limitation in terms of cost, read-length, and throughput. In this regard, DNA sequencing by synthesis (SBS), where the identity of each nucleotide is detected immediately after its incorporation into a growing strand of DNA in a polymerase reaction, offers an alternative approach to address some of these limitations. An important requirement for the SBS approach is a 3'-OH capped fluorescent nucleotide that can act as a reversible terminator (2), where after the identification of the nucleotide incorporated in a DNA polymerase reaction, the 3'-OH capping group along with fluorescent label are removed to regenerate a free 3'-OH group thus allowing DNA chain elongation. The importance of removing the fluorescent label after each base identification is to make sure that the residual fluorescence from the previous nucleotide incorporation does not affect the identification of the next incorporated fluorescent nucleotide.

The speed and sequence read length of SBS depend on the yield of the cleavage efficiency of the fluorophore and the allyl group. Due to multiple steps required in the identification, removal of fluorescent label, and regeneration of 3'-OH group after each nucleotide incorporation in SBS, the loss of even a minor efficiency at each step may lead to inhibition of prolonged read length. For this reason, any improvement in efficiency within each cycle of nucleotide identification, fluorophore removal, and 3'-OH regeneration can have significant impact on read length, thus tackling the physical limits in DNA sequencing by synthesis.

SUMMARY

This invention provides a nucleotide analogue comprising (i) a base selected from the group consisting of adenine or an analogue of adenine, guanine or an analogue of guanine, cytosine or an analogue of cytosine, thymine or an analogue of thymine and uracil or an analogue of uracil, (ii) a deoxyribose, (iii) an allyl moiety bound to the 3'-oxygen of the deoxyribose and (iv) a fluorophore bound to the base via an allyl linker.

This invention also provides a method for making a nucleotide analogue wherein the nucleotide analogue comprises (i) a base selected from the group consisting of adenine or an analogue of adenine, guanine or an analogue of guanine, cytosine or an analogue of cytosine and uracil or an analogue of uracil, (ii) a deoxyribose, (iii) an allyl moiety bound to the 3' oxygen of the deoxyribose, and (iv) a fluorophore bound to the base via an allyl linker which is not an iso-allyl linker, comprising the steps of:

(a) contacting 6-amino-hex-2-en-1-ol and an N-hydroxysuccinimide ester of a fluorophore in the presence of a first suitable solvent and a suitable base;

(b) treating the resulting product of step (a) with DSC/Et$_3$N in a second suitable solvent; and (c) treating the resulting product of step (b) with a 3'-O-allyl-dNTP-NH$_2$ in the presence of a suitable buffered solvent, wherein the base of the 3'-O-allyl-dNTP-NH$_2$ is an adenine, guanine, cytosine, uracil, or an analogue thereof, thereby making the nucleotide analogue.

This invention also provides a method for making a nucleotide analogue wherein the nucleotide analogue comprises (i) a base selected from the group consisting of adenine or an analogue of adenine, guanine or an analogue of guanine, cytosine or an analogue of cytosine and uracil or an analogue of uracil, (ii) a deoxyribose, (iii) an allyl moiety bound to the 3' oxygen of the deoxyribose, and (iv) a fluorophore bound to the base via an allyl linker, comprising the steps of:

(a) contacting 2-(2-amino-ethyl)-prop-2-en-1-ol and an N-hydroxysuccinimide ester of a fluorophore in the presence of a first suitable solvent and a suitable base;

(b) treating the resulting product of step (a) with DSC/Et$_3$N in a second suitable solvent; and (c) treating the resulting product of step (b) with a 3'-O-allyl-dNTP-NH$_2$ in the presence of a suitable buffered solvent, wherein the base of the 3'-O-allyl-dNTP-NH$_2$ is an adenine, guanine, cytosine, uracil, or an analogue thereof, thereby making the nucleotide analogue.

This invention also provides a method for determining the sequence of a DNA comprising performing the following steps for each residue of the DNA to be sequenced:

(a) contacting the DNA with a DNA polymerase in the presence of (i) a primer and (ii) four fluorescent nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) an allyl moiety bound to the 3'-oxygen of the deoxyribose and (iv) a fluorophore bound to the base via an allyl linker, so that a nucleotide analogue complementary to the residue being sequenced is bound to the DNA by the DNA polymerase, and (3) each of the four analogues has a predetermined fluorescence wavelength which is different than the fluorescence wavelengths of the other three analogues;

(b) removing unbound nucleotide analogues;

(c) determining the identity of the bound nucleotide analogue; and (d) following step (c), except with respect to the final DNA residue to be sequenced, chemically cleaving from the bound nucleotide analogue the fluorophore and the allyl moiety bound to the 3'-oxygen atom of the deoxyribose, thereby determining the sequence of the DNA.

This invention also provides a kit for performing the instant method comprising, in separate compartments, (a) a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, (ii) a deoxyribose, (iii) an allyl moiety bound to the 3'-oxygen of the deoxyribose and (iv) a fluorophore bound to the base via an allyl linker,
(b) reagents suitable for use in DNA polymerization; and
(c) instructions for use.

This invention also provides a method for covalently affixing a detectable moiety, via an allyl linker, to an $NH_2$-bearing molecule, comprising contacting the detectable moiety with the $NH_2$-bearing molecule in the presence of a suitable solvent and suitable base, wherein the detectable moiety comprises a mass tag, fluorophore or chromophore bound to a NHS ester of an allyl moiety. In one embodiment of the $NH_2$-bearing molecule is a nucleotide and the detectable moiety comprises a fluorophore.

DETAILED DESCRIPTION OF THE INVENTION

Terms

Figure 1:
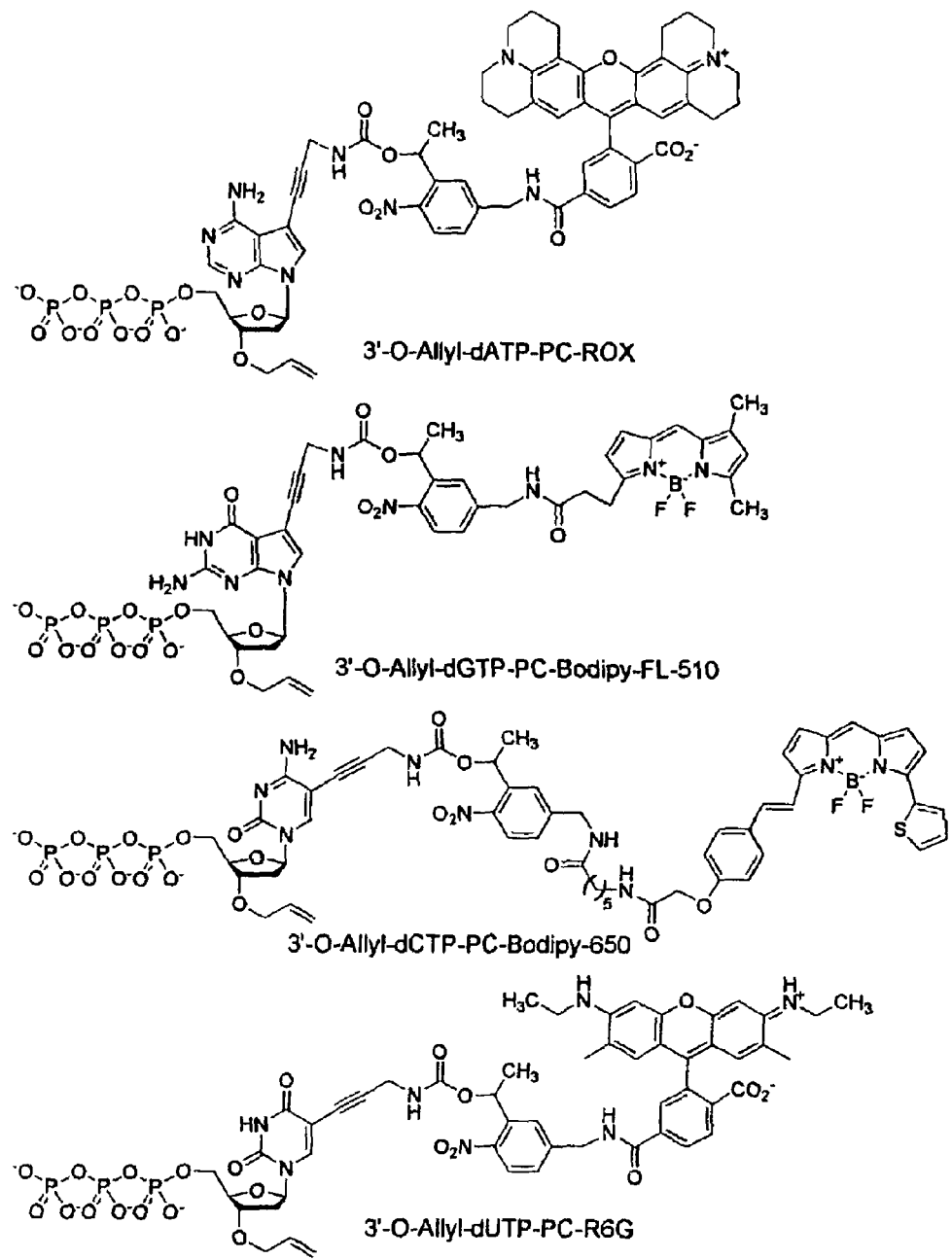
FIG. 1: Structures of four 3'-O-allyl-dNTP-PC-fluorophores.

The following definitions are presented as an aid in understanding this invention:
A—Adenine;
C—Cytosine;
DNA—Deoxyribonucleic acid;
DMF—Dimethylformamide;
G—Guanine;
NHS—N-hydroxysuccinimidyl;
RNA—Ribonucleic acid;
SBS—Sequencing by synthesis;
T—Thymine; and
U—Uracil.

"Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996 1997, Roche Molecular Systems, Inc., Branchburg, N.J., USA).

As used herein, "self-priming moiety" shall mean a nucleic acid moiety covalently bound to a nucleic acid to be transcribed, wherein the bound nucleic acid moiety, through its proximity with the transcription initiation site of the nucleic acid to be transcribed, permits transcription of the nucleic acid under nucleic acid polymerization-permitting conditions (e.g. the presence of a suitable polymerase, nucleotides and other reagents). That is, the self-priming moiety permits the same result (i.e. transcription) as does a non-bound primer. In one embodiment, the self-priming moiety is a single stranded nucleic acid having a hairpin structure.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

As used herein, "nucleotide analogue" shall mean an analogue of A, G, C, T or U (that is, an analogue of a nucleotide comprising the base A, G, C, T or U) which is recognized by DNA or RNA polymerase (whichever is applicable) and incorporated into a strand of DNA or RNA (whichever is appropriate). Examples of nucleotide analogues include, without limitation 7-deaza-adenine, 7-deaza-guanine, the analogues of deoxynucleotides shown in FIG. 6, analogues in which a label is attached through a cleavable linker to the 5-position of cytosine or thymine or to the 7-position of deaza-adenine or deaza-guanine, analogues in which a small chemical moiety such as —$CH_2OCH_3$ or —$CH_2CH\!=\!CH_2$ is used to cap the —OH group at the 3'-position of deoxyribose, and analogues of related dideoxynucleotides. Nucleotide analogues, including dideoxynucleotide analogues, and DNA polymerase-based DNA sequencing are also described in U.S. Pat. No. 6,664,079.

1,3 dipolar azide-alkyne cycloaddition chemistry is described in WO 2005/084367 and PCT/US03/39354, the contents of each of which are hereby incorporated by reference.

All embodiments of U.S. Pat. No. 6,664,079 (the contents of which are hereby incorporated by reference) with regard to sequencing a nucleic acid are specifically envisioned here.

With regard to the synthesis of the nucleotide analogues disclosed herein, other fluorophores or chromophores to be cleavably attached to the base of the analogue are envisioned. In addition, combinatorial fluorescence energy tags as described in U.S. Pat. No. 6,627,748 (the contents of which are hereby incorporated by reference) or mass tags may be used in place of the fluorophores described herein.

EMBODIMENTS OF THE INVENTION

This invention provides a nucleotide analogue comprising (i) a base selected from the group consisting of adenine or an analogue of adenine, guanine or an analogue of guanine, cytosine or an analogue of cytosine, thymine or an analogue of thymine and uracil or an analogue of uracil, (ii) a deoxyribose, (iii) an allyl moiety bound to the 3'-oxygen of the deoxyribose and (iv) a fluorophore bound to the base via an allyl linker.

In one embodiment, the nucleotide analogue is an analogue of dATP, dGTP, dCTP or dUTP. In one embodiment, the fluorophore is selected from the group consisting of ROX, Bodipy-FL-510, Bodipy-650 and R6G. In one embodiment, the fluorophore is bound to the base via an iso-allyl linker.

In a further embodiment, the nucleotide analogue is selected from the group consisting of 3'-O-allyl-dGTP-iso-allyl-Bodipy-FL-510, 3'-O-allyl-dCTP-iso-allyl-Bodipy-650, 3'-O-allyl-dATP-iso-allyl-ROX and 3'-O-allyl-dUTP-iso-allyl-R6G, or is selected from the group consisting of 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G.

This invention also provides a method for making a nucleotide analogue wherein the nucleotide analogue comprises (i) a base selected from the group consisting of adenine or an analogue of adenine, guanine or an analogue of guanine, cytosine or an analogue of cytosine and uracil or an analogue of uracil, (ii) a deoxyribose, (iii) an allyl moiety bound to the 3' oxygen of the deoxyribose, and (iv) a fluorophore bound to the base via an allyl linker which is not an iso-allyl linker, comprising the steps of:
(a) contacting 6-amino-hex-2-en-1-ol and an N-hydroxysuccinimide ester of a fluorophore in the presence of a first suitable solvent and a suitable base;
(b) treating the resulting product of step (a) with DSC/$Et_3N$ in a second suitable solvent; and
(c) treating the resulting product of step (b) with a 3'-O-allyl-dNTP-$NH_2$ in the presence of a suitable buffered solvent, wherein the base of the 3'-O-allyl-dNTP-$NH_2$ is an adenine, guanine, cytosine, uracil, or an analogue thereof, thereby making the nucleotide analogue.

Figure 2:
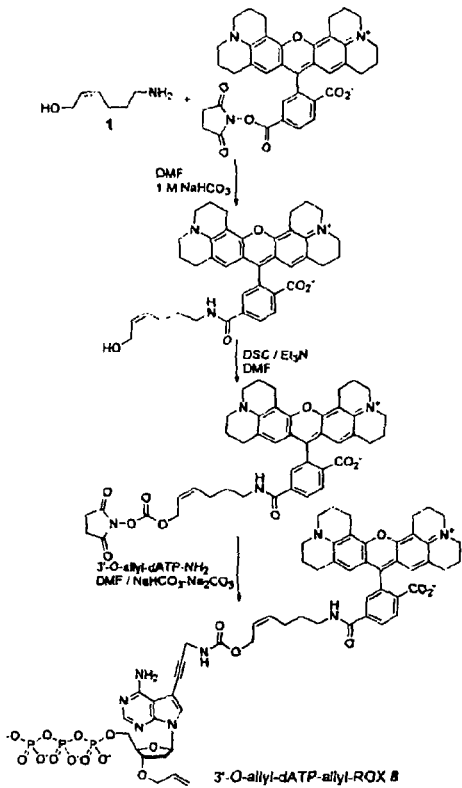
FIG. 2. Synthesis of 3'-O-allyl-dNTP-allyl-fluorophores.
Figure 2:
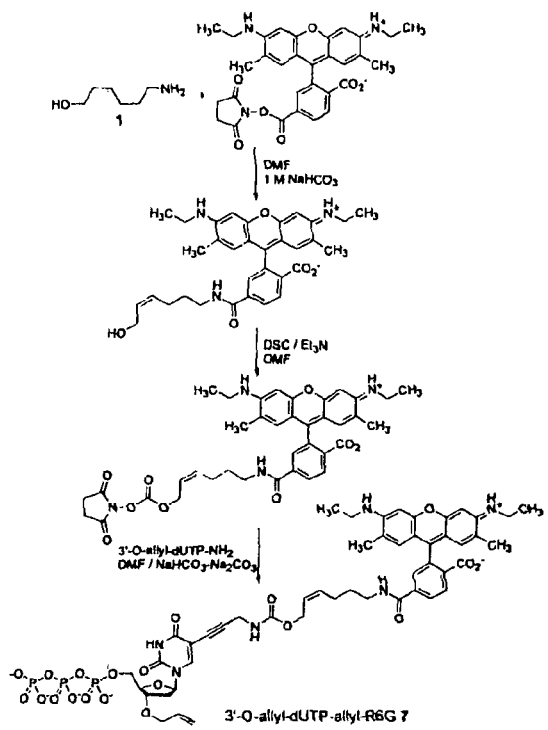
Figure 2:
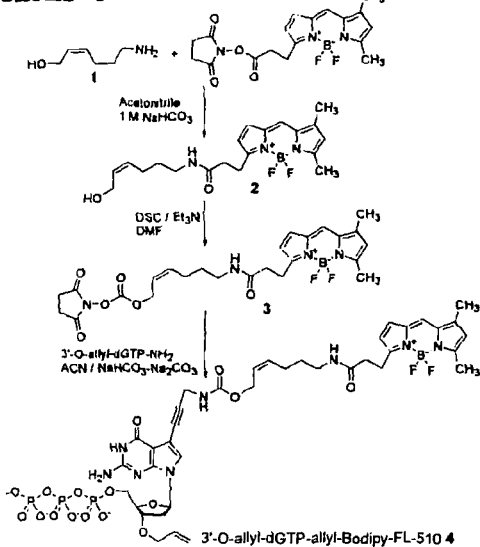
Figure 2:
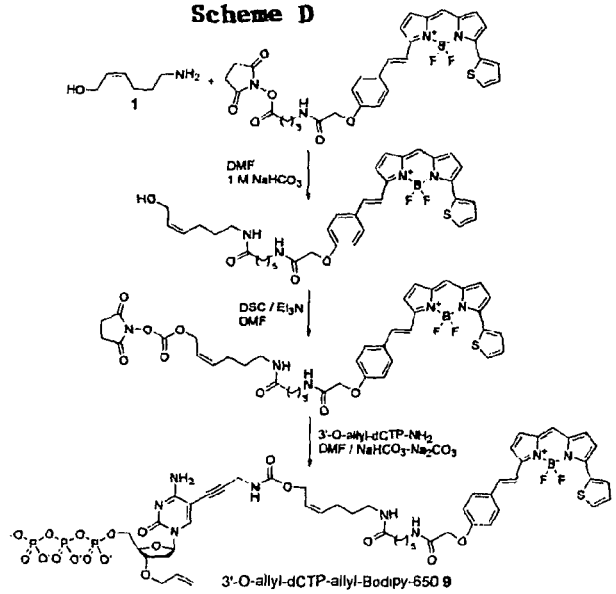

In one embodiment, the steps of the instant method comprise those set forth in FIG. 2, scheme A; FIG. 2, scheme B; FIG. 2, scheme C; or FIG. 2, scheme D.

In one embodiment of the instant method, the first suitable solvent is DMF and the second suitable solvent is DMF, and in another embodiment the first suitable solvent is acetonitrile and the second suitable solvent is DMF. In one embodiment of the instant method, the suitable base is $NaHCO_3$. In one embodiment of the instant method, the suitable buffered solvent is DMF buffered with $NaHCO_3$—$Na_2CO_3$. In another embodiment of the instant method, the suitable buffered solvent is acetonitrile buffered with $NaHCO_3$—$Na_2CO_3$.

This invention also provides a method for making a nucleotide analogue wherein the nucleotide analogue comprises (i) a base selected from the group consisting of adenine or an analogue of adenine, guanine or an analogue of guanine, cytosine or an analogue of cytosine and uracil or an analogue of uracil, (ii) a deoxyribose, (iii) an allyl moiety bound to the 3' oxygen of the deoxyribose, and (iv) a fluorophore bound to the base via an allyl linker, comprising the steps of:
(a) contacting 2-(2-amino-ethyl)-prop-2-en-1-ol and an N-hydroxysuccinimide ester of a fluorophore in the presence of a first suitable solvent and a suitable base;
(b) treating the resulting product of step (a) with DSC/$Et_3N$ in a second suitable solvent; and
(c) treating the resulting product of step (b) with a 3'-O-allyl-dNTP-$NH_2$ in the presence of a suitable buffered solvent, wherein the base of the 3'-O-allyl-dNTP-$NH_2$ is an adenine, guanine, cytosine, uracil, or an analogue thereof, thereby making the nucleotide analogue.

Figure 6:
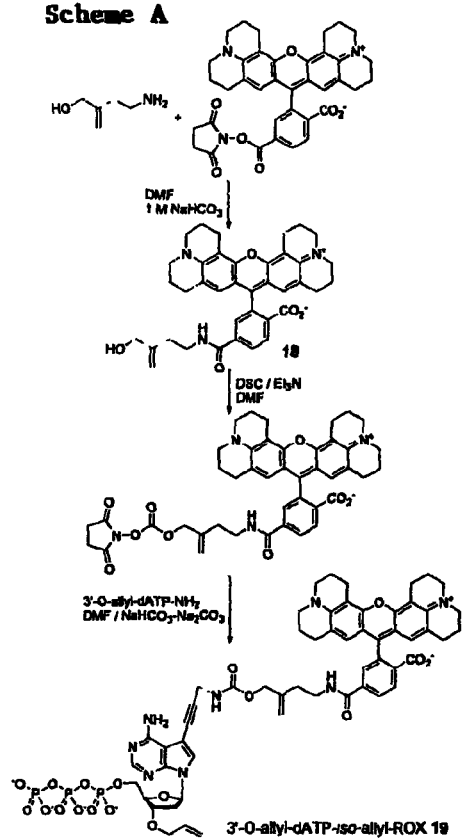
FIG. 6. Synthesis of 3'-O-allyl-dNTP-iso-allyl-fluorophore.
Figure 6:
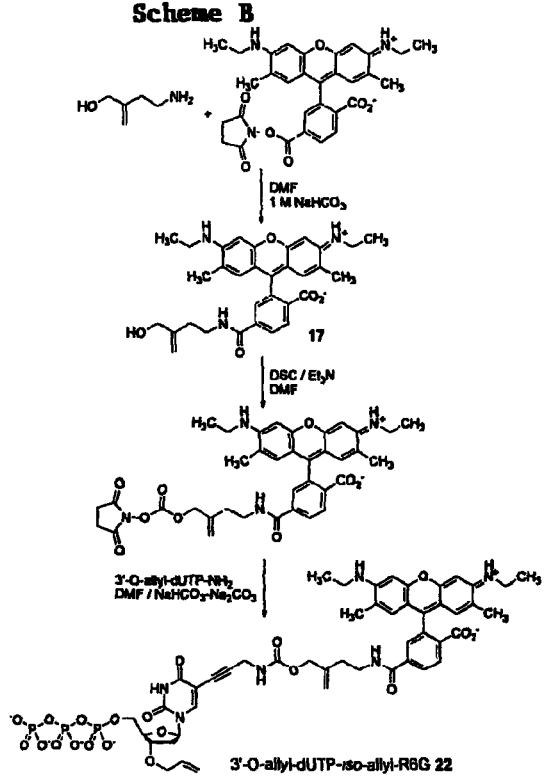
Figure 6:
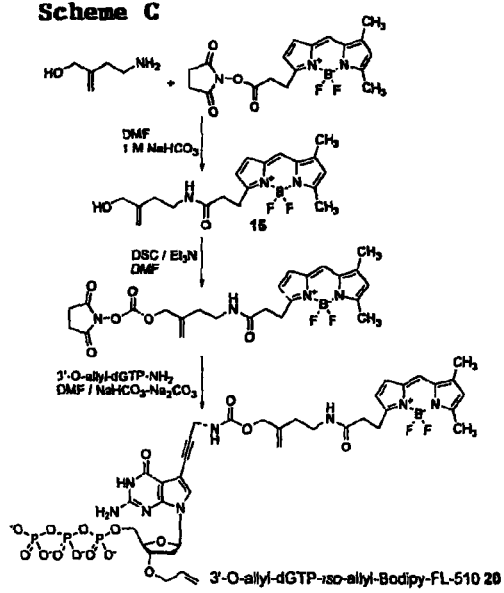
Figure 6:
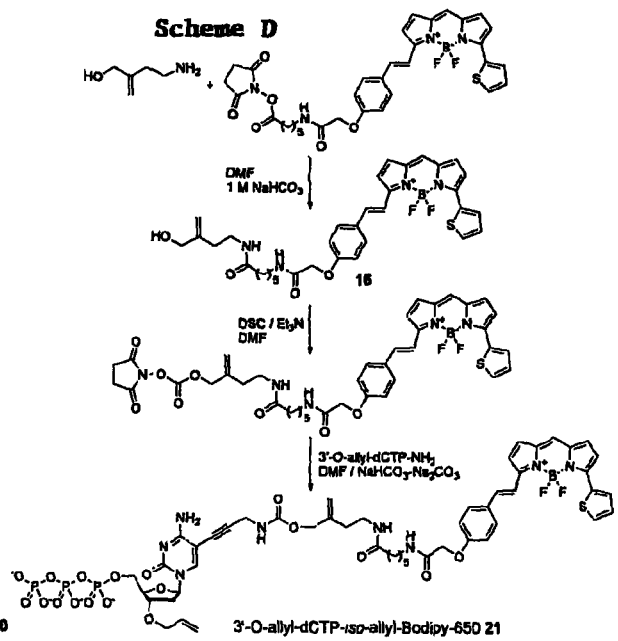

In one embodiment of the instant method, the steps comprise those set forth in FIG. 6, scheme A; FIG. 6, scheme B; FIG. 6, scheme C; or FIG. 6, scheme D.

In one embodiment of the instant method, the first suitable solvent is DMF and the second suitable solvent is DMF. In one embodiment of the instant method, the suitable base is $NaHCO_3$. In one embodiment of the instant method, the suitable buffered solvent is DMF buffered with $NaHCO_3$—$Na_2CO_3$.

This invention also provides a method for determining the sequence of a DNA comprising performing the following steps for each residue of the DNA to be sequenced:
(a) contacting the DNA with a DNA polymerase in the presence of (i) a primer and (ii) four fluorescent nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) an allyl moiety bound to the 3'-oxygen of the deoxyribose and (iv) a fluorophore bound to the base via an allyl linker, so that a nucleotide analogue complementary to the residue being sequenced is bound to the DNA by the DNA polymerase, and (3) each of the four analogues has a predetermined fluorescence wavelength which is different than the fluorescence wavelengths of the other three analogues;
(b) removing unbound nucleotide analogues;
(c) determining the identity of the bound nucleotide analogue; and
(d) following step (c), except with respect to the final DNA residue to be sequenced, chemically cleaving from the bound nucleotide analogue the fluorophore and the allyl moiety bound to the 3'-oxygen atom of the deoxyribose, thereby determining the sequence of the DNA.

In one embodiment of the instant method, chemically cleaving the fluorophore and the allyl moiety bound to the 3'-oxygen atom is performed using $Na_2PdCl_4$.

In one embodiment of the instant method, the primer is a self-priming moiety.

In one embodiment of the instant method, the DNA is bound to a solid substrate. In one embodiment of the instant method, the DNA is bound to the solid substrate via 1,3-dipolar azide-alkyne cycloaddition chemistry. In one embodiment of the instant method, about 1000 or fewer copies of the DNA are bound to the solid substrate.

In one embodiment of the instant method, the four fluorescent nucleotide analogues are 3'-O-allyl-dGTP-iso-allyl-Bodipy-FL-510, 3'-O-allyl-dCTP-iso-allyl-Bodipy-650, 3'-O-allyl-dATP-iso-allyl-ROX and 3'-O-allyl-dUTP-iso-allyl-R6G.

In another embodiment of the instant method, the four fluorescent nucleotide analogues are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G.

In one embodiment of the instant method, the DNA polymerase is a 9°N polymerase.

This invention also provides a kit for performing the instant method comprising, in separate compartments,
(a) a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, (ii) a deoxyribose, (iii) an allyl moiety bound to the 3'-oxygen of the deoxyribose and (iv) a fluorophore bound to the base via an allyl linker,
(b) reagents suitable for use in DNA polymerization; and
(c) instructions for use.

In one embodiment, the kit comprises 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G.

In one embodiment, the kit comprises 3'-O-allyl-dGTP-iso-allyl-Bodipy-FL-510, 3'-O-allyl-dCTP-iso-allyl-Bodipy-650, 3'-O-allyl-dATP-iso-allyl-ROX and 3'-O-allyl-dUTP-iso-allyl-R6G.

This invention also provides a method for covalently affixing a detectable moiety, via an allyl linker, to an $NH_2$-bearing molecule, comprising contacting the detectable moiety with the $NH_2$-bearing molecule in the presence of a suitable solvent and suitable base, wherein the detectable moiety comprises a mass tag, fluorophore or chromophore bound to a NHS ester of an allyl moiety. In one embodiment, the $NH_2$-bearing molecule is a nucleotide and the detectable moiety comprises a fluorophore.

In an embodiment, the allyl is chemically cleaved using a palladium catalyst. In an embodiment the cleaving is performed using $Na_2PdCl_4$ and TPPTS. In one embodiment the pH is between 8.5 and 9. In a further embodiment the pH is 8.8.

In embodiments of this invention, the sequencing methods described can be applied, mutatis mutandis, to sequencing an RNA molecule or an RNA/DNA hybrid molecule.

This invention will be better understood by reference to the Experimental Details which follow, but those skilled in the art will readily appreciate that the specific experiments detailed are only illustrative of the invention as described more fully in the claims which follow thereafter.

Experimental Details

Synopsis

Here, the construction of a novel chemically cleavable fluorescent labeling system based on an allyl group to modify nucleotides for DNA sequencing by synthesis (SBS) is explored. It is found that an allyl moiety can be used successfully as a linker to tether a fluorophore to a 3'-O-allyl-modified nucleotides (A, C, G, U), forming chemical cleavable reversible terminators, 3'-O-allyl-dNTP-allyl-fluorophore, for application in SBS. The fluorophore and the 3'-O-allyl group on a DNA extension product, which is generated by incorporating 3'-O-allyl-dNTP-allyl-fluorophore, are removed simultaneously in 30 sec by Pd-catalyzed deallylation in aqueous buffer solution. This one-pot dual-deallylation reaction thus allows the re-initiation of the polymerase reaction and increases the SBS efficiency. Expansion of this novel linker and selective protection strategy to other applications that include bio-conjugation, solution- and solid-phase organic synthesis is envisaged.

Introduction

A disulfide group has been previously explored as a chemically cleavable linker to attach a fluorophore to a deoxynucleotide and the use of 2-mercaptoethanol to remove the fluorophore after the nucleotide incorporation and detection in SBS (4). However, the disulfide bond can be reversed and destabilized under certain conditions (5, 6). Here, the construction of a novel chemically cleavable fluorescent labeling system based on an allyl group is disclosed. The discovery permits fluorophore linker cleaving the 3'-O-allyl capping group removal in a single step, thus increasing SBS efficiency. Disclosed here is an allyl moiety that can be used successfully as a linker to tether a fluorophore to a 3'-O-allyl-capped nucleotide, thus forming a set of chemical cleavable reversible terminators, 3'-O-allyl-dNTP-allyl-fluorophores (FIG. 2).

The fluorophore and the 3'-O-allyl group on a DNA extension product which is generated by incorporating structure 4 (FIG. 2) are removed simultaneously in 30 sec by Pd-catalyzed deallylation in aqueous buffer solution. This one-pot dual-deallylation reaction thus allows the re-initiation of the polymerase reaction. Design, synthesis and evaluation of a 3'-O-allyl fluorescent nucleotide, 3'-O-allyl-dGTP-allyl-Bodipy-FL-510 (structure 4) with a fluorophore attached to the 7 position of guanine base via an allyl carbamate linker, and its application as a reversible terminator for SBS is shown in FIG. 3.

Readily available allylic alcohol (structure 1) was chosen as a starting material for the preparation of 4. First, allylic alcohol 1 was reacted with N-hydroxysuccinimide (NHS) ester of the BODIPY-FL-510 to produce allylic-Bodipy-FL-510-NHS (structure 2), which was subsequently converted to its corresponding NHS ester (structure 3) by reacting with N,N'-disuccinimidyl carbonate. The coupling reaction between 3 and the modified nucleotide (3'-O-allyl-dGTP-$NH_2$) (3) produced the chemically cleavable fluorescent nucleotide, 3'-O-allyl-dGTP-allyl-Bodipy-FL-510 4.

Figure 3:
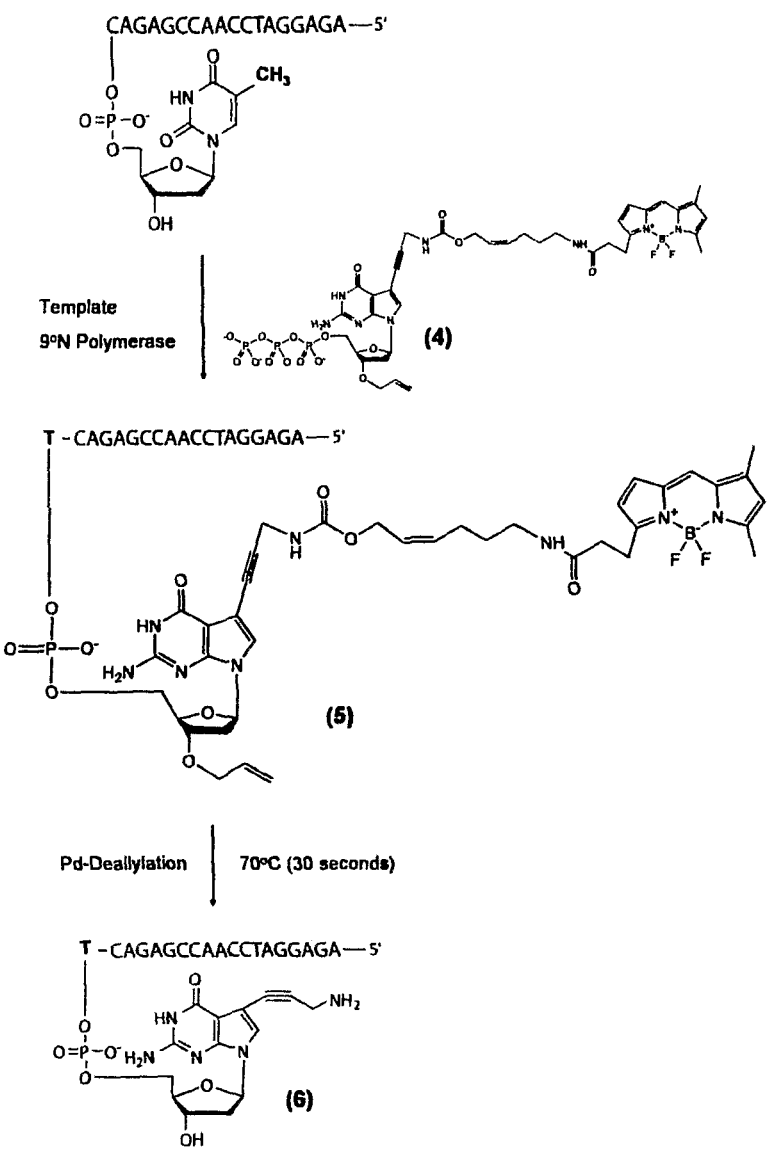
FIG. 3. Polymerase DNA extension reaction using 3'-O-allyl-dGTP-allyl-Bodipy-FL-510 as a reversible terminator.
Figure 4:
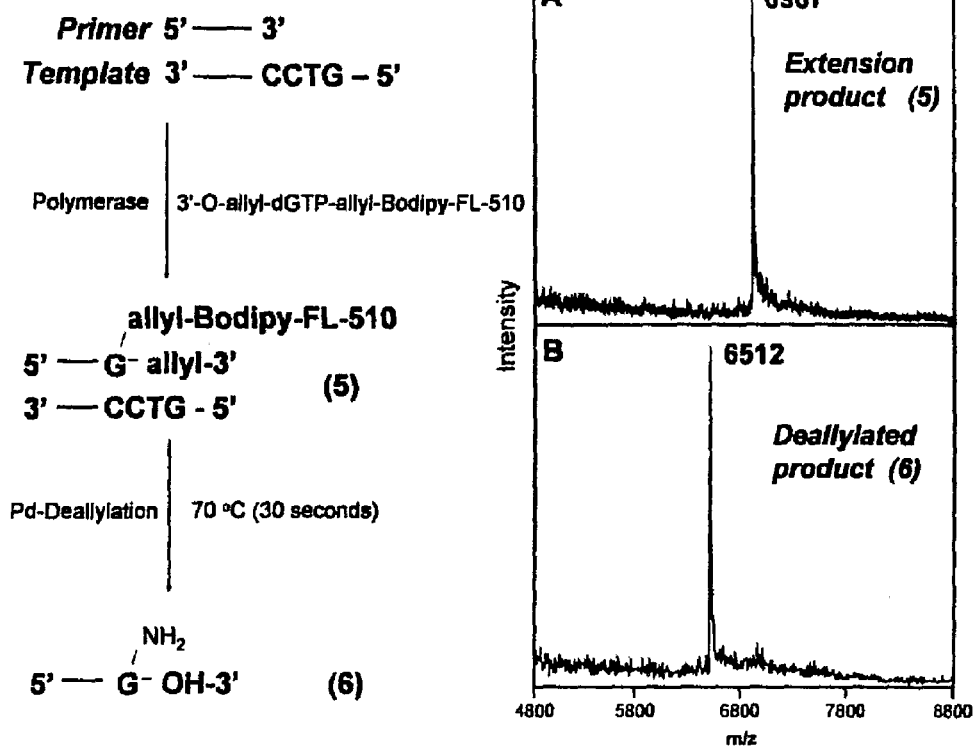
FIG. 4. A polymerase extension scheme (left) and MALDI-TOF MS spectra of extension and dual-deallylation product (right).

To verify that 3'-O-allyl-dGTP-allyl-Bodipy-FL-510 4, acting as a reversible terminator, is incorporated accurately in a base-specific manner in a polymerase reaction, a polymerase DNA extension reaction was performed in solution as shown in FIG. 3. This allows the isolation of the DNA product at each step for detailed molecular structure characterization by using MALDI-TOF MS as shown in FIG. 4. First, a polymerase extension reaction using 3'-O-allyl-dGTP-allyl-Bodipy-FL-510 4 as a terminator along with a primer and the synthetic 100-mer DNA template corresponding to a portion of exon 7 of the human p53 gene was performed producing a single-base extension product (structure 5). After the reaction, a small portion of the DNA extension product 5 was characterized by MALDI-TOF MS. The rest of the extended DNA product 5 was added to a deallylation cocktail [1× Thermopol reaction buffer/$Na_2PdCl_4$/$P(PhSO_3Na)_3$] to perform dual-deallylation in a one-pot reaction for 30 sec to yield deallylated DNA product 6 and characterized by MALDI-TOF MS. The deallylated DNA product with both the fluorophore removed and a free 3'-OH group regenerated can then be used as a primer for a next nucleotide extension reaction.

FIG. 4 (right panel) shows sequential mass spectrum at each step of DNA sequencing by synthesis using 3'-O-allyl-dGTP-allyl-Bodipy-FL-510 4 as a reversible terminator. As can be seen from FIG. 4A, the MALDI-TOF MS spectrum consists of a distinct peak at m/z 6,967 corresponding to the single base DNA extension product 5 with 100% incorporation efficiency, confirming that the reversible terminator 4 can be incorporated base-specifically by DNA polymerase into a growing DNA strand. FIG. 4B shows the one-pot dual-deallylation result after 30 sec incubation of the DNA extension product in a deallylation cocktail solution. The peak at m/z 6,967 has completely disappeared, whereas the peak at m/z 6,512 corresponding to a DNA product 6 with both the fluorophore and 3'-O-allyl removed appears as the sole product. The absence of a peak at m/z 6,967 proves that the one-pot dual-deallylation reaction in removing both the fluorophore and the 3'-O-allyl group from the DNA product was completed with high efficiency. Furthermore, the allyl linker moiety is completely stable in a polymerase extension condition and can be selectively cleaved in a rapid and efficient manner.

Figure 5:
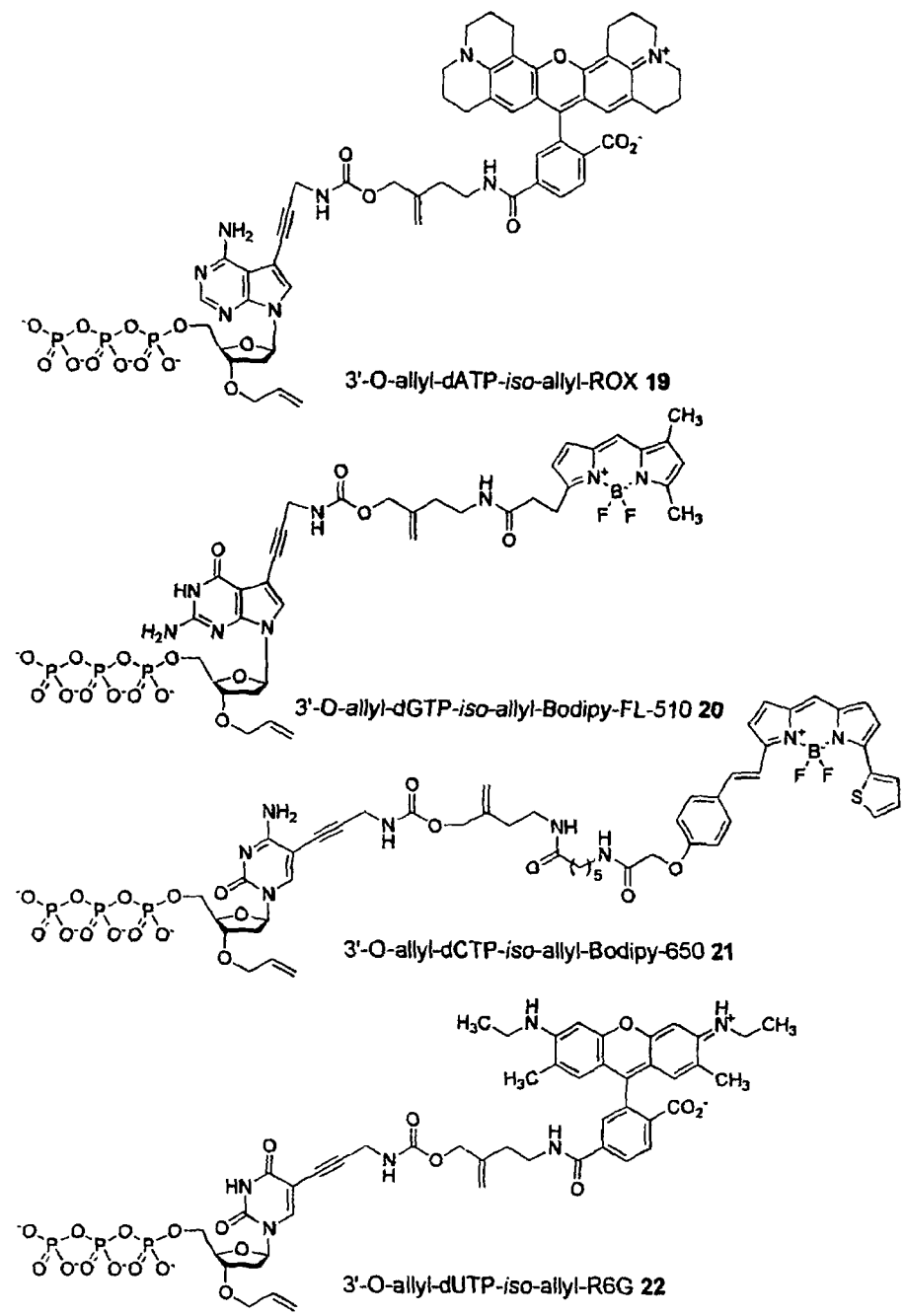
FIG. 5. Structures of four alternative chemically cleavable fluorescent nucleotides, 3'-O-allyl-dNTP-iso-allyl-fluorophore.
Figure 7:
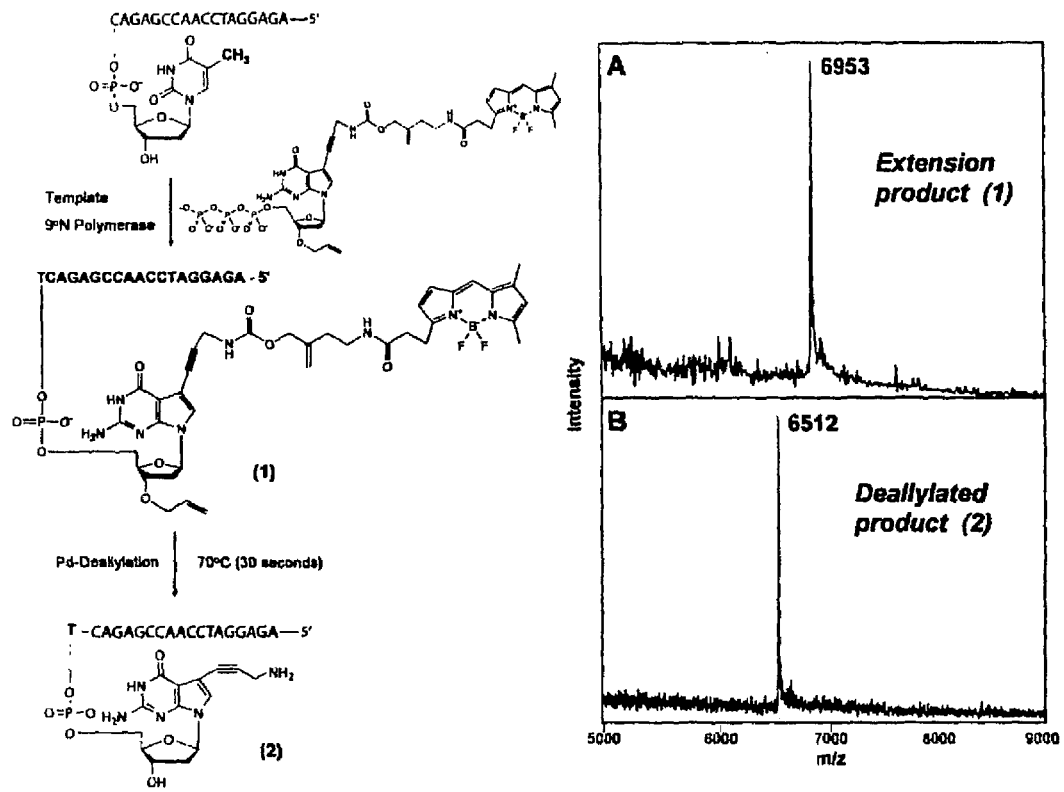
FIG. 7. A polymerase extension scheme (left) and MALDI-TOF MS spectra of extension and dual-deallylation product (right).

Another version of the allyl linker for the construction of the chemically cleavable fluorescent nucleotides as reversible terminators was investigated. The structures of the four molecules (3'-O-allyl-dNTP-iso-allyl-fluorophore) are shown in FIG. 5. The syntheses of these molecules are shown in FIG. 6. As an example, the polymerase extension scheme using 3'-O-allyl-dGTP-iso-allyl-Bodipy-FL-510 as a reversible terminator and the corresponding MALDI-TOF MS results are shown in FIG. 7. The other three chemically fluorescent nucleotides (A, C, U) are similarly characterizable by MALDI-TOF MS.

The experimental results show that the 3'-O-allyl-dNTP-allyl-fluorophore can be faithfully incorporated into a growing DNA strand in a polymerase extension reaction to act as reversible terminators in SBS. This novel linker and selective protection strategy can be applied to other tasks that include bio-conjugation, solution- and solid-phase organic synthesis.
Material and Methods General Information. $^1$H NMR spectra were recorded on a Brucker DPX-400 (400 MHz) spectrometer and are reported in ppm from $CD_3OD$ or $CDCl_3$ internal standard (3.31 or 7.26 ppm respectively). Data are reported as follows: (s=singlet, d=doublet, t=triplet, q=quartet, m=multiplet, coupling constant(s) in Hz; integration; assignment). Proton decoupled $^{13}$C NMR spectra were recorded on a Brucker DPX-400 (100 MHz) spectrometer and are reported in ppm from $CD_3OD$ or $CDCl_3$ internal standard (49.0 or 77.0 ppm respectively). High Resolution Mass Spectra (HRMS) were obtained on a JEOL JMS HX 110A mass spectrometer. Mass measurement of DNA was made on a Voyager DE MALDI-TOF mass spectrometer (Applied Biosystems). The NHS esters of the fluorophores were purchased from Molecular Probes. All other chemicals were purchased from Sigma-Aldrich. 9°N polymerase (exo-) A485L/Y409V was generously provided by New England Biolabs.

Synthesis of Chemically Cleavable Linker:
6-Amino-Hexen-1-ol (1)

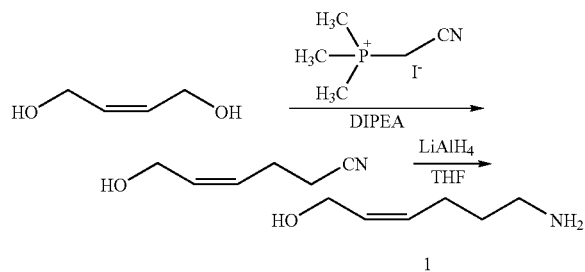

To a mixture of (cis)-2-butene-1,4-diol (440 mg, 5.00 mmol) and (cyanomethyl)-trim ethylphosphonium iodide (1.24 g, 5.10 mmol) (Zaragoza, F. J. Org. Chem. 2002; 67(14), 4963-4964) were added propionitrile (4.0 mL) and N,N'-diisopropylethylamine (DIPEA) (1.10 mL, 6.32 mmol), and the mixture was stirred at 97° C. for 24 h. Water (0.20 mL, 11.1 mmol) was added, and stirring at 97° C. was continued for 15 h. Water (25 mL) and concentrated hydrochloric acid (1.0 mL, 12 mmol) were added, and the mixture was extracted with ethyl acetate (3×25 mL). The combined extracts were washed with brine, dried with $Na_2SO_4$, and concentrated. The residue was purified by flash chromatography to yield 410 mg (74%) 6-hydroxy-4-hexanenitrile as an oil. $^1$H NMR (400 MHz, $CDCl_3$) δ 5.71 (m, 1H), 5.62 (m, 1H), 4.20 (d, 2H), 2.45 (t, 2H), 2.33 (q, 2H). $^{13}$C NMR (100 MHz, $CDCl_3$) δ 129.3, 129.1, 117.7, 60.0, 22.5, 18.3. HRMS m/z: calcd for $C_6H_9NO$ (M+H$^+$) 112.068, found 112.082.

To a suspension of $LiAlH_4$ (380 mg, 10.0 mmol) in THF (50 mL) was added slowly dropwise a solution of 6-hydroxy-4-hexanenitrile (333 mg, 3.00 mmol) in THF (20 mL) while keeping the temperature below 0° C. When the reaction slowed down, the mixture was heated to reflux for 24 h. The excess $LiAlH_4$ was quenched by addition of 15% sodium hydroxide. The resulting white precipitate was filtered. The filtrate was dried over $Na_2SO_4$ and concentrated under reduced pressure to yield 6-Amino-hexen-1-ol 1 (296 mg, 85%) as yellow oil. $^1$H NMR (400 MHz, $CDCl_3$) δ 1.54 (q, 2H), 1.82 (brs, 3H, $NH_2$+OH), 5.71 (m, 1H), 5.62 (m, 1H), 4.20 (d, 2H), 4.07 (d, 2H), 2.70 (t, 2H), 2.09 (q, 2H). $^{13}$C NMR (100 MHz, $CDCl_3$) δ 132.3, 129.8, 63.6, 41.8, 32.2, 29.8. HRMS m/z calcd for $C_6H_{14}NO$ (M+H$^+$) 117.075, found 117.107.

Allylic-Bodipy-FL-510 (2).

Allylic alcohol (1) (3 mg, 0.026 mmol) was dissolved in 550 μl of acetonitrile and 100 μl of 1 M $NaHCO_3$ aqueous solution. A solution of Bodipy-FL-510 N-hydroxysuccinimidyl (NHS) ester (5 mg, 0.013 mmol) in 400 μl of acetonitrile was added slowly to the above reaction mixture and then stirred for 5 h at room temperature. The resulting reaction mixture was purified on a preparative silica-gel TLC plate ($CHCl_3/CH_3OH$=95:5) to give pure allylic-Bodipy-FL-510 (2) (4.8 mg, 46%). $^1$H NMR (400 MHz, $CD_3OD$) δ 7.50 (s, 1H), 6.63 (s, 1H), 6.33 (s, 1H), 5.68 (m, 1H), 5.62 (m, 1H), 5.45 (m, 2H), 4.21 (d, 2H), 3.23 (t, 2H), 2.24 (t, 2H), 2.22 (t, 2H), 2.16 (d, 1H), 2.05 (d, 1H), 2.00 (m, 2H), 1.57 (m, 2H). $^{13}$C NMR (100 MHz, $CD_3OD$) δ 175.4, 163.7, 146.9, 145.8, 132.1, 130.0, 129.2, 128.7, 123.2, 116.0, 109.2, 101.0, 59.4, 40.4, 34.0, 30.6, 30.3, 24.8, 18.7, 16.9. High-resolution MS (FAB$^+$) m/z: anal. calcd for $C_{20}H_{26}O_2N_3F_2B$ (M+H$^+$), 390.2086; found, 390.2101.

Allylic-Bodipy-FL-510 NHS Ester (3).

N,N'-disuccinimidyl carbonate (4.27 mg, 0.017 mmol) and triethylamine (4.6 μl, 0.033 mmol) were added to a solution of allylic-Bodipy-FL-510 (2) (4.8 mg, 0.012 mmol) in 200 μl of dry acetonitrile. The reaction mixture was stirred under argon at room temperature for 6 h. Solvent was removed under vacuum, and 1 ml of 1 M $NaHCO_3$ aqueous solution was added to the residual mixture. Extracted with ethyl acetate three times, the combined organic layer was dried over $Na_2SO_4$, which was directly subjected to the following coupling reaction without further purification.

3'-O-allyl-dGTP-allyl-Bodipy-FL-510 (4)

Crude allylic-Bodipy-FL-510 NHS ester (3) (6.3 mg) in 300 μl of acetonitrile was added to a solution of 3'-O-allyl-dGTP-NH$_2$ (2 mg, 0.004 mmol) in 300 μl of $Na_2CO_3$/$NaHCO_3$ buffer (0.1 M, pH 8.7). The reaction mixture was stirred at room temperature for 3 h, which was subsequently purified by preparative silica-gel TLC plate ($CHCl_3/CH_3OH$, 1/1) to remove unreacted allylic-Bodipy-FL-510 NHS ester (3). The crude product was concentrated further under vacuum and purified with reverse-phase HPLC on a 150×4.6-mm C18 column to obtain the pure product 3'-O-allyl-dGTP-allyl-Bodipy-FL-510 (4) (retention time of 35 min). Mobile phase: A, 8.6 mM triethylamine/100 mM hexafluoroisopropyl alcohol in water (pH 8.1); B, methanol. Elution was performed with 100% A isocratic over 10 min, followed by a linear gradient of 0-50% B for 20 min and then 50% B isocratic over another 20 min. 4 was characterized by the following primer extension reaction and MALDI-TOF MS.

Primer Extension Using
3'-O-allyl-dGTP-allyl-Bodipy-FL-510 (4)

The polymerase extension reaction mixture consisted of 60 μmol of primer (5'-GTTGAT-GTACACATTGTCAA-3') (SEQ ID NO:1), 80 pmol of 100-mer template (5'-TACCCG- GAGGC-CAAGTACGGCGGGTACGTCCTTGACAAT-GTGTACATCAACATCACCTACCACCATGT CAGTCTCGGTTGGATCCTCTATTGTGTCCGGG-3') (SEQ ID NO:2), 120 pmol of 3'-O-allyl-dGTP-allyl-Bodipy-FL-510 (4), 1× Thermopol reaction buffer (20 mM Tris-HCl/ 10 mM $(NH_4)_2SO_4$/10 mM KCl/2 mM $MgSO_4$/0.1% Triton X-100, pH 8.8, New England Biolabs), and 6 units of 9°N Polymerase (exo-)A485L/Y409V in a total volume of 20 µl. The reaction consisted of 20 cycles at 94° C. for 20 sec, 46° C. for 40 sec, and 60° C. for 90 sec. After the reaction, a small portion of the DNA extension product was desalted by using ZipTip and analyzed by MALDI-TOF MS, which shows a dominant peak at m/z 6,967 corresponding to the DNA product (5). The rest of the product 5 was subjected to the following deallylation.

One-Pot Dual-Deallylation of DNA Extension Product (5) to Produce DNA Product (6)

DNA product 5 (20 pmol) was added to a mixture of degassed 1× Thermopol reaction buffer (20 mM Tris-HCl/10 mM $(NH_4)_2SO_4$/10 mM KCl/2 mM $MgSO_4$/0.1% Triton X-100, pH 8.8, 1 µl), $Na_2PdCl_4$ in degassed $H_2O$ (7 µl, 23 nmol) and $P(PhSO_3Na)_3$ in degassed $H_2O$ (10 µl, 176 nmol) to perform a one-pot dual-deallylation reaction. The reaction mixture was then placed in a heating block and incubated at 70° C. for 30 seconds to yield quantitatively deallylated DNA product (6) and analyzed by MALDI-TOF MS to yield a single peak at m/z 6,512.

3'-O-allyl-dUTP-allyl-R6G (7)

Crude Allylic-R6G NHS ester (prepared by the same procedure as Allylic-Bodipy-FL-510 NHS ester) (7 mg) in 300 µl of DMF was added to a solution of 3'-O-allyl-dUTP-$NH_2$ (2 mg, 4 mmol) in 300 µl of $Na_2CO_3$—$NaHCO_3$ buffer (0.1 M, pH 8.7). The reaction mixture was stirred at room temperature for 3 h. A preparative silica-gel TLC plate was used to purify the crude product ($CHCl_3$/$CH_3OH$, 1/1). The resulting product was concentrated under vacuum and further purified with reverse-phase HPLC on a 150×4.6-mm C18 column to obtain the pure product 10 (retention time of 38 min). Mobile phase: A, 8.6 mM triethylamine/100 mM hexafluoroisopropyl alcohol in water (pH 8.1); B, methanol. Elution was performed with 100% A isocratic over 10 min, followed by a linear gradient of 0-50% B for 20 min and then 50% B isocratic over another 20 min. 3'-O-allyl-dUTP-allyl-R6G was characterized by single-base extension reaction and MALDI-TOF MS similarly as for 4.

3'-O-allyl-dATP-allyl-ROX (8)

Crude Allylic-ROX NHS ester (prepared by the same procedure as Allylic-Bodipy-FL-510 NHS ester) (7 mg) in 300 µl of DMF was added to a solution of 3'-O-allyl-dATP-$NH_2$ (2 mg, 4 mmol) in 300 µl of $Na_2CO_3$—$NaHCO_3$ buffer (0.1 M, pH 8.7). The reaction mixture was stirred at room temperature for 3 h. A preparative silica-gel TLC plate was used to purify the crude product ($CHCl_3$/$CH_3OH$, 1/1). The resulting product was concentrated under vacuum and further purified with reverse-phase HPLC on a 150×4.6-mm C18 column to obtain the pure product 10 (retention time of 40 min). Mobile phase: A, 8.6 mM triethylamine/100 mM hexafluoroisopropyl alcohol in water (pH 8.1); B, methanol. Elution was performed with 100% A isocratic over 10 min, followed by a linear gradient of 0-50% B for 20 min and then 50% β isocratic over another 20 min. 3'-O-allyl-dATP-allyl-ROX was characterized by single-base extension reaction and MALDI-TOF MS similarly as for 4.

3'-O-allyl-dCTP-allyl-Bodipy-650 (9)

Crude Allylic-Bodipy-650 NHS ester (prepared by the same procedure as Allylic-Bodipy-FL-510 NHS ester) (7 mg) in 300 µl of DMF was added to a solution of 3'-O-allyl-dCTP-$NH_2$ (2 mg, 4 µmol) in 300 µl of $Na_2CO_3$—$NaHCO_3$ buffer (0.1 M, pH 8.7). The reaction mixture was stirred at room temperature for 3 h. A preparative silica-gel TLC plate was used to purify the crude product ($CHCl_3$/$CH_3OH$, 1/1). The resulting product was concentrated under vacuum and further purified with reverse-phase HPLC on a 150×4.6-mm C18 column to obtain the pure product 10 (retention time of 35 min). Mobile phase: A, 8.6 mM triethylamine/100 mM hexafluoroisopropyl alcohol in water (pH 8.1); B, methanol. Elution was performed with 100% A isocratic over 10 min, followed by a linear gradient of 0-50% B for 20 min and then 50% β isocratic over another 20 min. 3'-O-allyl-dCTP-allyl-Bodipy-650 was characterized by single-base extension reaction and MALDI-TOF MS similarly as for 4.

Synthesis of Chemically Cleavable Linker 4-Amino-2-methylene-1-butanol (14):

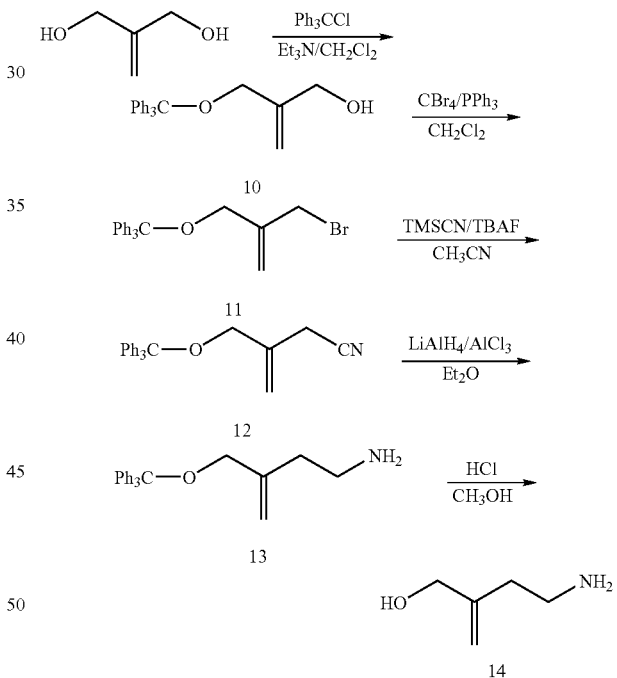

2-triphenylmethoxymethyl-2-propen-1-ol (10)

To a solution of trityl chloride (4.05 g; 14.3 mmol) and 2-methylenepropane-1,3-diol (1.20 mL; 14.3 mmol) in dry $CH_2Cl_2$ (20 mL) was added triethylamine (4.0 mL; 28.5 mmol) slowly at room temperature. The reaction was stirred at room temperature for 1 h and then ethyl acetate (100 mL) and saturated aqueous $NaHCO_3$ (30 mL) were added. The organic layer was separated and washed by saturated aqueous $NaHCO_3$ and NaCl respectively, and dried over anhydrous $Na_2SO_4$. After evaporation of the solvent, the residue was purified by flash column chromatography over silica gel using ethyl acetate-hexane (1:10~5) as the eluent to afford 10 as white solid (2.89 g; 62% yield): $^1$H NMR (400 MHz, CDCl$_3$) δ 7.42-7.48 (m, 6H, six of ArH), 7.27-7.33 (m, 6H, six of ArH), 7.20-7.27 (m, 3H, three of ArH), 5.26 (s, 1H, one of C=CH$_2$), 5.17 (s, 1H, one of C=CH$_2$), 4.13 (d, J=6.1 Hz, 2H, CH$_2$OH), 3.70 (s, 2H, Ph$_3$COCH$_2$), 1.72 (t, J=6.1 Hz, 1H, CH$_2$OH); $^{13}$C NMR (100 MHz, CDCl$_3$) δ 145.4, 143.6, 128.3, 127.6, 126.8, 111.6, 87.0, 65.3, 64.5, (8).

1-bromo-2-triphenylmethoxymethyl-2-propene (11)

To a solution of 10 (2.56 g; 7.74 mmol) in CH$_2$Cl$_2$ (75 ml), CBr$_4$ (3.63 g; 10.83 mmol) and triphenylphosphine (2.47 g; 9.31 mmol) were added respectively at 0° C. and the reaction was stirred at room temperature for 40 min. Cooled to 0° C., ethyl acetate (100 mL) and saturated aqueous NaHCO$_3$ (30 mL) were added. The organic layer was separated and washed by saturated aqueous NaCl, and dried over anhydrous Na$_2$SO$_4$. After evaporation of the solvent, the residue was purified by flash column chromatography over silica gel using CH$_2$Cl$_2$-hexane (1:5) as the eluent to afford 11 as white solid (3.02 g; 92% yield): $^1$H NMR (400 MHz, CDCl$_3$) δ 7.42-7.48 (m, 6H, six of ArH), 7.27-7.33 (m, 6H, six of ArH), 7.20-7.27 (m, 3H, three of ArH), 5.37 (s, 1H, one of C=CH$_2$), 5.31 (s, 1H, one of C=CH$_2$), 4.01 (s, 2H, CH$_2$Br), 3.75 (s, 2H, Ph$_3$COCH); $^{13}$C NMR (100 MHz, CDCl$_3$) δ 143.6, 142.6, 128.4, 127.6, 126.9, 115.8, 86.9, 64.2, 33.5, (9).

3-triphenylmethoxymethyl-3-butanenitrile (12)

To a solution of 11 (1.45 g; 3.69 mmol) and in dry CH$_3$CN (37 mL) was added trimethylsilyl cyanide (0.49 mL; 3.69 mmol). Then 1 M tetrabutylammonium fluoride (TBAF) in THF solution (3.69 mL, 3.69 mmol) was added slowly at room temperature and the reaction was stirred for 20 min. Most solvents were evaporated and ethyl acetate (100 mL) and saturated aqueous NaHCO$_3$ (30 mL) were added. The organic layer was washed by saturated aqueous NaCl and dried over anhydrous Na$_2$SO$_4$. After evaporation of the solvent, the residue was purified by flash column chromatography over silica gel using acetate-hexane (1:10) as the eluent to afford 12 as white solid (1.01 g; 64% yield): $^1$H NMR (400 MHz, CDCl$_3$) δ 7.39-7.45 (m, 6H, six of ArH), 7.21-7.34 (m, 9H, nine of ArH), 5.31 (s, 2H, C=CH$_2$), 3.64 (s, 2H, Ph$_3$COCH$_2$), 3.11 (s, 2H, CH$_2$CN); $^{13}$C NMR (100 MHz, CDCl$_3$) δ 143.3, 135.5, 128.2, 127.7, 126.9, 116.8, 114.7, 87.0, 65.7, 21.9, (10).

3-triphenylmethoxymethyl-3-buten-1-amine (13)

To a solution of LiAlH$_4$ (119 mg; 2.98 mmol) in dry ether (5 mL), AlCl$_3$ (400 mg; 2.94 mmol) was added carefully at 0° C. and the mixture was stirred for 15 min. Then a solution of 12 (829 mg; 2.44 mmol) in dry ether (9 mL) was added and the reaction was stirred at 0° C. for 3 h. After that 10% aqueous NaOH (10 mL) was added to quench the reaction. The organic layer was separated and washed by saturated aqueous NaHCO$_3$ and NaCl respectively, and dried over anhydrous K$_2$CO$_3$. After evaporation of the solvent, the residue was purified by flash column chromatography over silica gel using CH$_3$OH—CH$_2$Cl$_2$ (1:20~5) as the eluent to afford 10 as colorless oil (545 mg; 65% yield): $^1$H NMR (400 MHz, CDCl$_3$) δ 7.41-7.48 (m, 6H, six of ArH), 7.26-7.33 (m, 6H, six of ArH), 7.19-7.26 (m, 3H, three of ArH), 5.33 (s, 1H, one of C=CH$_2$), 4.96 (s, 1H, one of C=CH$_2$), 3.53 (s, 2H, Ph$_3$COCH$_2$), 2.70 (m, 2H, CH$_2$CH$_2$NH$_2$), 2.18 (t, J=6.7 Hz, 2H, CH$_2$CH$_2$NH$_2$), 2.06 (br s, 2H, NH$_2$); $^{13}$C NMR (100 MHz, CDCl$_3$) δ 143.6, 143.4, 128.1, 127.4, 126.5, 111.3, 86.5, 66.1, 39.8, 37.4; HRMS (FAB+) calcd for C$_{24}$H$_{26}$ON (M+H$^+$): 344.2014, found: 344.2017, (11).

4-amino-2-methylene-1-butanol (14)

To a solution of 13 (540 mg; 1.57 mmol) in CH$_3$OH (11 mL) was added HCl (2M solution in ether; 5.5 mL) at room temperature and the reaction was stirred for 1 h. Then 7 M methanolic ammonia solution (2.7 mL) was added at room temperature and the reaction was stirred for 10 min. The white solid formed was removed by filtration and washed by CH$_3$OH. The combined solution was evaporated the residue was purified by flash column chromatography over silica gel using CH$_3$OH—CH$_2$Cl$_2$ (1:4) as the eluent to afford 14 as colorless oil (151 mg; 95% yield): $^1$H NMR (400 MHz, CD$_3$OD) δ 5.19 (s, 1H, one of C=CH$_2$), 5.01 (s, 1H, one of C=CH$_2$), 4.06 (s, 2H, CH$_2$OH), 3.10 (t, J=7.5 Hz, 2H, CH$_2$CH$_2$NH$_2$), 2.46 (t, J=7.5 Hz, 2H, CH$_2$CH$_2$NH$_2$); $^{13}$C NMR (100 MHz, CD$_3$OD) δ 145.3, 113.7, 65.5, 39.5, 32.0.

The synthetic procedures of iso-allylic-fluorophore, iso-allylic-fluorophore NHS ester and 3'-O-allyl-dNTP-iso-allyl-fluorophore are the same as described previously for allylic-fluorophore, allylic-fluorophore NHS ester, and 3'-O-allyl-dNTP-allyl-fluorophore, respectively.

iso-Allyl-Bodipy-FL-510 (15)

$^1$H NMR (400 MHz, CD$_3$OD) δ 7.42 (s, 1H), 7.00 (d, J=4.0 Hz, 1H), 6.32 (d, J=4.0 Hz, 1H), 6.21 (s, 1H), 5.06 (s, 1H, one of C=CH$_2$), 4.87 (s, 1H, one of C=CH$_2$), 4.01 (s, 2H, CH$_2$OH), 3.33 (t, J=7.5 Hz, 2H), 3.21 (t, J=7.7 Hz, 2H), 2.59 (t, J=7.7 Hz, 2H), 2.51 (s, 3H, one of ArCH$_3$), 2.28 (s, 3H), 2.26 (t, J=7.1 Hz, 2H)

iso-Allyl-Bodipy-650 (16)

$^1$H NMR (400 MHz, CD$_3$OD) δ 8.12 (dd, J=0.9, 3.8 Hz, 1H), 7.63 (m, 3H), 7.54 (d, J=6.4 Hz, 2H), 7.35 (s, 1H), 7.18-7.22 (m, 2H), 7.12 (m, 2H), 7.06 (d, J=8.8 Hz, 2H), 6.85 (d, J=4.2 Hz, 1H), 5.06 (s, 1H, one of C=CH$_2$), 4.86 (s, 1H, one of C=CH$_2$), 4.56 (s, 2H), 4.00 (s, 2H, CH$_2$OH), 3.28 (m, 4H), 2.23 (t, J=7.1 Hz, 2H), 2.14 (t, J=7.5 Hz, 2H), 1.49-1.62 (m, 4H), 1.25-1.34 (m, 2H).

iso-Allyl-R6G (17)

$^1$H NMR (400 MHz, CD$_3$OD) δ 8.12 (d, J=8.1 Hz, 1H), 8.05 (dd, J=1.8, 8.1 Hz, 1H), 7.66 (d, J=1.6 Hz, 1H), 7.02 (s, 2H), 6.88 (s, 2H), 5.08 (s, 1H, one of C=CH$_2$), 4.92 (s, 1H, one of C=CH$_2$), 4.06 (s, 2H, CH$_2$OH), 3.48-3.56 (m, 6H), 2.40 (t, J=7.2 Hz, 2H), 2.13 (s, 6H), 1.36 (t, J=7.2 Hz, 6H).

iso-Allyl-ROX (18)

$^1$H NMR (400 MHz, CD$_3$OD) δ 8.03 (d, J=8.1 Hz, 1H), 7.98 (dd, J=1.6, 8.1 Hz, 1H), 7.60 (d, J=1.4 Hz, 1H), 6.75 (s, 2H), 5.08 (s, 1H, one of C=CH$_2$), 4.91 (s, 1H, one of C=CH$_2$), 4.05 (s, 2H, CH$_2$OH), 3.45-3.57 (m, 10H), 3.03-3.10 (m, 4H), 2.64-2.73 (m, 4H), 2.38 (t, J=7.1 Hz, 2H), 2.04-2.15 (m, 4H), 1.89-1.99 (m, 4H).

REFERENCES

1. Collins, F. S.; Green, E. D.; Guttmacher, A. E.; Guyer, M. S. "A vision for the future of genomics research". *Nature* 2003, 422, 835-847.
2. Ju, J.; Li, Z.; Edwards, J.; Itagaki, Y. "Massive parallel method for decoding DNA and RNA". U.S. patent 2003, U.S. Pat. No. 6,664,079.
3. Meng, Q.; Kim, D. H.; Bai, X.; Bi, L.; Turro, N. J.; Ju, J. "Design and synthesis of a photocleavable fluorescent nucleotide 3'-O-allyl-dGTP-PC-Bodipy-FL-510 as a reversible terminator for DNA sequencing by synthesis". *JACS*, submitted
4. Mitra, R. D.; Shendure, J.; Olejnik, J.; Olejnik, E. K.; Church, G. M. "Fluorescent in situ sequencing on polymerase colonies". *Anal. Biochem.* 2003, 320, 55-65.
5. Pleasants, J. C.; Guo, W.; Rabenstein, D. L. "A comparative study of the kinetics of selenol/diselenide and thiol/disulfide exchange reactions". *J. Am. Chem. Soc.* 1989, 111, 6553-6558.
6. Huyghues-Despointes, B. M. P.; Nelson, J. W. "Stabilities of disulfide bond intermediates in the folding of apamin". *Biochemistry* 1992, 31, 1476-1483.
7. Ruparel, H.; Li, Z.; Bai, X.; Kim, D. H.; Turro, N. J.; Ju, J. "Design and synthesis of a 3'-O-allyl photocleavable fluorescent nucleotide as a reversible terminator for DNA sequencing by synthesis". *Proc. Natl. Acad. Sci. USA* 2005, 102, 5932-5937.
8. Kang, J.-H.; Siddiqui, M. A.; Sigano, D. M.; Krajewski, K.; Lewin, N. E.; Pu, Y.; Blumberg, P. M.; Lee, J. and Marquez, V. E. Conformationally constrained analogues of diacylglycerol. 24. Asymmetric synthesis of a chiral (R)-DAG-Lactone template as a versatile precursor for highly functionalized DAG-Lactones. *Org. Lett.* 2004, 6(14), 2413-2416
9. Honma, M.; Sawada, T.; Fujisawa, Y.; Utsugi, M.; Watanabe, H.; Umino, A.; Matsumura, T.; Hagihara, T.; Takano, M. and Nakada, M. Asymmetric catalysis on the intramolecular cyclopropanation of α-diazo-β-keto Sulfones *J. Am. Chem. Soc.* 2003, 125(10), 2860-2861.
10. Soli, E. D.; Manoso, A. S.; Patterson, M. C. and DeShong, P. Azide and cyanide displacements via hypervalent silicate intermediates *J. Org. Chem.* 1999, 64(9), 3171-7.
11. Jacobson, M. A. and Williard, P. G. Generation of 1-azapentadienyl anion from N-(tert-butyldimethylsilyl)-3-buten-1-amine *J. Org. Chem.* 2002, 67(11), 3915-3918.

What is claimed is:

1. A nucleotide analogue comprising (i) a base selected from the group consisting of adenine or an analogue of adenine, guanine or an analogue of guanine, cytosine or an analogue of cytosine, thymine or an analogue of thymine and uracil or an analogue of uracil, (ii) a deoxyribose, (iii) an allyl moiety bound to the 3'-oxygen of the deoxyribose and (iv) a fluorophore bound to the base via an iso-allyl linker.

2. The nucleotide analogue of claim 1, wherein the nucleotide analogue is an analogue of dATP, dGTP, dCTP or dUTP.

3. The nucleotide analogue of claim 1, wherein the fluorophore is selected from the group consisting of ROX, Bodipy-FL-510, Bodipy-650 and R6G.

4. The nucleotide analogue of claim 1, wherein the nucleotide analogue is selected from the group consisting of 3'-O-allyl-dGTP-iso-allyl-Bodipy-FL-510, 3'-O-allyl-dCTP-iso-allyl-Bodipy-650, 3'-O-allyl-dATP-iso-allyl-ROX and 3'-O-allyl-dUTP-iso-allyl-R6G.

5. A method for making a nucleotide analogue wherein the nucleotide analogue comprises (i) a base selected from the group consisting of adenine or an analogue of adenine, guanine or an analogue of guanine, cytosine or an analogue of cytosine and uracil or an analogue of uracil, (ii) a deoxyribose, (iii) an allyl moiety bound to the 3° oxygen of the deoxyribose, and (iv) a fluorophore bound to the base via an iso-allyl linker, comprising the steps of:

(a) contacting 2-(2-amino-ethyl)-prop-2-en-1-ol and an N-hydroxysuccinimide ester of a fluorophore in the presence of a first suitable solvent and a suitable base to produce an iso-allyl-fluorophore;

(b) treating the resulting product of step (a) with DSC/Et$_3$N in a second suitable solvent; and (c) treating the resulting product of step (b) with a 3'-O-allyl-dNTP-NH$_2$ in the presence of a suitable buffered solvent, wherein the base of the 3'-O-allyl-dNTP-NH$_2$ is an adenine, guanine, cytosine, uracil, or an analogue thereof, thereby making the nucleotide analogue.

6. The method of claim 5, wherein the steps comprise those set forth in FIG. 6, scheme A; FIG. 6, scheme B; FIG. 6, scheme C; or FIG. 6, scheme D.

7. The method of claim 5, wherein the first suitable solvent is DMF and the second suitable solvent is DMF.

8. The method of claim 5, wherein the suitable base is $NaHCO_3$.

9. The method of claim 5, wherein the suitable buffered solvent is DMF buffered with $NaHCO_3$—$Na_2CO_3$.

10. A method for determining the sequence of a DNA comprising performing the following steps for each residue of the DNA to be sequenced:
   (a) contacting the DNA with a DNA polymerase in the presence of (i) a primer and (ii) four fluorescent nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of DATP, (2) each nucleotide analogue comprises (i) a base selected from the group consisting of adenine, guanine, cytosine, thymine or uracil, and analogues thereof, (ii) a deoxyribose, (iii) an allyl moiety bound to the 3'-oxygen of the deoxyribose and (iv) a fluorophore bound to the base via an iso-allyl linker, so that a nucleotide analogue complementary to the residue being sequenced is bound to the DNA by the DNA polymerase, and (3) each of the four analogues has a predetermined fluorescence wavelength which is different than the fluorescence wavelengths of the other three analogues;
   (b) removing unbound nucleotide analogues;
   (c) determining the identity of the bound nucleotide analogue; and
   (d) following step (c), except with respect to the final DNA residue to be sequenced, chemically cleaving from the bound nucleotide analogue the fluorophore and the allyl moiety bound to the 3'-oxygen atom of the deoxyribose, thereby determining the sequence of the DNA.

11. The method of claim 10, wherein chemically cleaving the fluorophore and the allyl moiety bound to the 3'-oxygen atom is performed using $Na_2PdCl_4$.

12. The method of claim 10, wherein the primer is a self-priming moiety.

13. The method of claim 10, wherein the DNA is bound to a solid substrate.

14. The method of claim 13, wherein the DNA is bound to the solid substrate via 1,3-dipolar azide-alkyne cycloaddition chemistry.

15. The method of claim 13, wherein about 1000 or fewer copies of the DNA are bound to the solid substrate.

16. The method of claim 10, wherein the four fluorescent nucleotide analogues are 3'-O-allyl-dFTP-iso-allyl-Bodipy-FL-510, 3'-O-allyl-dCTP-iso-allyl-Bodipy-650, 3'-O-allyl-dATP-iso-allyl-ROX and 3'-O-allyl-dUTP-iso-allyl-R6G.

17. The method of claim 10, wherein the DNA polymerase is a 9°N polymerase.

18. A kit for performing the method claim 10, comprising, in separate compartments,
   (a) a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, (ii) a deoxyribose, (iii) an allyl moiety bound to the 3'-oxygen of the deoxyribose and (iv) a fluorophore bound to the base via an iso-allyl linker,
   (b) reagents suitable for use in DNA polymerization; and
   (c) instructions for use.

19. The kit of claim 18, wherein the kit comprises 3'-O-allyl-dGTP-iso-allyl-Bodipy-FL-510, 3'-O-allyl-dCTP-iso-allyl-Bodipy-650, 3'-O-allyl-dATP-iso-allyl-ROX and 3'-O-allyl-dUTP-iso-allyl-R60.

* * * * *

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer directed to Human p53

<400> SEQUENCE: 1
gttgatgtac acattgtcaa                                              20

<210> SEQ ID NO 2
<211> LENGTH: 100
<212> TYPE: DNA
<213> ORGANISM: Homo sapiens

<400> SEQUENCE: 2
tacccggagg ccaagtacgg cgggtacgtc cttgacaatg tgtacatcaa catcacctac   60
caccatgtca gtctcggttg gatcctctat tgtgtccggg                        100
```